United States Patent
Ward et al.

(10) Patent No.: US 10,335,547 B2
(45) Date of Patent: Jul. 2, 2019

(54) METHOD AND APPARATUS FOR CLOSED-LOOP CONTROL OF NERVE ACTIVATION

(71) Applicant: PURDUE RESEARCH FOUNDATION, West Lafayette, IN (US)

(72) Inventors: Matthew P. Ward, West Lafayette, IN (US); Pedro Irazoqui, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/349,511

(22) PCT Filed: Oct. 24, 2012

(86) PCT No.: PCT/US2012/061687
§ 371 (c)(1),
(2) Date: Apr. 3, 2014

(87) PCT Pub. No.: WO2013/063111
PCT Pub. Date: May 2, 2013

(65) Prior Publication Data
US 2014/0243714 A1   Aug. 28, 2014

Related U.S. Application Data

(60) Provisional application No. 61/550,584, filed on Oct. 24, 2011.

(51) Int. Cl.
A61B 5/00 (2006.01)
A61B 5/04 (2006.01)
(Continued)

(52) U.S. Cl.
CPC ............. *A61M 5/1723* (2013.01); *A61B 5/04* (2013.01); *A61B 5/4035* (2013.01);
(Continued)

(58) Field of Classification Search
CPC ............................. A61N 7/00; A61H 23/0245
See application file for complete search history.

(56) References Cited

U.S. PATENT DOCUMENTS

| 4,570,640 A | 2/1986 | Barsa |
| 6,066,163 A | 5/2000 | John |

(Continued)

FOREIGN PATENT DOCUMENTS

| KR | 20130119620 A | 11/2013 |
| WO | WO-2011/051955 A2 | 5/2011 |

OTHER PUBLICATIONS

"About Treatment Resistant Depression", VNS Therapy, Cyberonics, ed.(2007).
(Continued)

*Primary Examiner* — Hien N Nguyen
(74) *Attorney, Agent, or Firm* — Marshall, Gerstein & Borun LLP; Randall G. Rueth

(57) ABSTRACT

The present disclosure is directed to a method and apparatus to autonomously stimulate a plurality of nerve fiber groups. The method and apparatus predicts stimulus parameters that can activate 0-100% of the nerve fiber groups selectively according to a patient's characteristics and proportional to therapeutic outcomes, such as determined by experimental data. The method and apparatus may further be configured to input experimental third-party data to obtain a high efficacy from a patient without invasive neurosurgery.

11 Claims, 19 Drawing Sheets

(51) Int. Cl.
 A61N 1/36 (2006.01)
 A61N 5/06 (2006.01)
 A61N 7/00 (2006.01)
 A61M 5/172 (2006.01)
(52) U.S. Cl.
 CPC .......... *A61B 5/4836* (2013.01); *A61N 1/3615* (2013.01); *A61N 1/36053* (2013.01); *A61N 1/36139* (2013.01); *A61N 1/36167* (2013.01); *A61N 5/0622* (2013.01); *A61N 7/00* (2013.01); *A61N 1/36171* (2013.01); *A61N 1/36175* (2013.01); *A61N 2007/0026* (2013.01)

(56) References Cited

U.S. PATENT DOCUMENTS

| 2005/0033378 | A1* | 2/2005 | Sheffield | A61N 1/36082 607/45 |
| 2005/0075701 | A1 | 4/2005 | Shafer | |
| 2005/0182453 | A1* | 8/2005 | Whitehurst | A61N 1/37205 607/45 |
| 2006/0135998 | A1 | 6/2006 | Libbus et al. | |
| 2006/0190053 | A1* | 8/2006 | Dobak, III | A61N 1/36167 607/44 |
| 2007/0027498 | A1 | 2/2007 | Maschino et al. | |
| 2007/0167984 | A1 | 7/2007 | Kieval et al. | |
| 2016/0367808 | A9* | 12/2016 | Simon | A61N 1/36064 |

OTHER PUBLICATIONS

Alesci et al., Major depression is associated with significant diurnal elevations in plasma interleukin-6 levels, a shift of its circadian rhythm, and loss of physiological complexity in its secretion: clinical implications, J. Clin. Endocrinol. Metab., 90(5):2522-30 (2005).
Allain et al., Enzymatic determination of total serum cholesterol, Clin. Chem., 20(4):470-5 (1974).
Bajbouj et al., Motor cortex excitability after vagus nerve stimulation in major depression, J. Clin. Psychopharmacol., 27(2):156-9 (2007).
Ballenger et al., Carbamazepine in manic-depressive illness: a new treatment, Am. J. Psychiatry, 138(7):782-90 (1980).
Behrend et al., Toward feedback controlled deep brain stimulation: dynamics of glutamate release in the subthalamic nucleus in rats, J. Neurosci. Methods, 180(2):278-89 (2009).
Ben-Menachem et al., Effects of vagus nerve stimulation on amino acids and other metabolites in the CSF of patients with partial seizures, Epilepsy Res., 20(3):221-7 (1995).
Ben-Menachem et al., Vagus nerve stimulation for treatment of partial seizures: 1. A controlled study of effect on seizures. First International Vagus Nerve Stimulation Study Group, Epilepsia, 35(3):616-26 (1994).
Bernik et al., Pharmacological stimulation of the cholinergic antiinflammatory pathway, J. Exp. Med., 195(6):781-8 (2002).
Besedovsky et al., Immune-neuroendocrine interactions, J. Immunol., 135(2 suppl):750s-4s (1985).
Bhagwagar et al., Persistent reduction in brain serotonin1A receptor binding in recovered depressed men measured by positron emission tomography with [11C]WAY-100635, Mol. Psychiatry, 9(4):386-92 (2004).
Blalock et al., The immune system: our mobile brain?, Immunol. Today, 6(4):115-7 (1985).
Blalock, The immune system as a sensory organ, J. Immunol., 132(3):1067-70 (1984).
Borovikova et al., Vagus nerve stimulation attenuates the systemic inflammatory response to endotoxin, Nature, 405(6785):458-62 (2000).
Bostock et al., The spatial distribution of excitability and membrane current in normal and demyelinated mammalian nerve fibres, J. Physiol., 341:41-58 (1983).
Bostock et al., Threshold tracking techniques in the study of human peripheral nerve, Muscle Nerve, 21(2):137-58 (1998).
Bostock, The strength-duration relationship for excitation of myelinated nerve: computed dependence on membrane parameters, J. Physiol., 341:59-74 (1983).
Brody et al., Regional brain metabolic changes in patients with major depression treated with either paroxetine or interpersonal therapy: preliminary findings, Arch. Gen. Psychiatry, 58(7):631-40 (2001).
Bruce, Comorbid depression in rheumatoid arthritis: pathophysiology and clinical implications, Curr. Psychiatry Rep., 10(3):258-64 (2008).
Campbell et al., Persistent pain and depression: a biopsychosocial perspective, Biol. Psychiatry, 54(3):399-409 (2003).
Cavaillon et al., Circulating cytokines: the tip of the iceberg?, Circ. Shock, 38(2):145-52 (1992).
Cizza et al., Elevated neuroimmune biomarkers in sweat patches and plasma of premenopausal women with major depressive disorder in remission: the POWER study, Biol. Psychiatry, 64(10):907-11 (2008).
Coyne et al., Prevalence, nature, and comorbidity of depressive disorders in primary care, Gen. Hosp. Psychiatry, 16(4):267-76 (1994).
Dantzer et al., From inflammation to sickness and depression: when the immune system subjgates the brain, Nat. Rev. Neurosci., 9:46-56 (2008).
Dantzer et al., Twenty years of research on cytokine-induced sickness behavior, Brain Behav. Immun., 21(2):153-60 (2007).
Dantzer, Cytokine-induced sickness behavior: mechanisms and implications, Ann. NY Acad. Sci., 933:222-34 (2001).
Das, Vagus nerve stimulation, depression, and inflammation, Neuropsychopharmacology, 32(9):2053-4 (2007).
Davidson et al., Depression: perspectives from affective neuroscience, Annu. Rev., 53:545-74 (2002).
De La Garza, Endotoxin- or pro-inflammatory cytokine-induced sickness behavior as an animal model of depression: focus on anhedonia, Neurosci. Biobehav. Rev., 29(4-5):761-70 (2005).
Di Lazzaro et al., Effects of vagus nerve stimulation on cortical excitability in epileptic patients, Neurology, 62(12):2310-2 (2004).
Dowlati et al., A meta-analysis of cytokines in major depression, Biol. Psychiatry, 67(5):446-57 (2010).
Dumitriu et al., Neurostimulatory therapeutics in management of treatment-resistant depression with focus on deep brain stimulation, Mt. Sinai J. Med., 75(3):263-75 (2008).
Ellis et al., Is platelet imipramine binding reduced in depression? A meta-analysis, Biol. Psychiatry, 36(5):292-9 (1994).
Evans et al., Intraoperative human vagus nerve compound action potentials, Acta. Psychiatrica Scandinavica, 11:232-8 (2004).
Evans et al., Mood disorders in the medically ill: scientific review and recommendations, Biol. Psychiatry, 58(3):175-89 (2005).
Fava et al., Folate, vitamin B12, and homocysteine in major depressive disorder, Am. J. Psychiatry, 154(3):426-8 (1997).
Feng et al., Toward closed-loop optimization of deep brain stimulation for Parkinson's disease: concepts and lessons from a computational model, J. Neural. Eng., 4(2):L14-21 (2007).
Foley et al., Quantitative studies of the vagus nerve in the cat. I. The ratio of sensory to motor fibers, J. Comp. Neurol., 67:49-97 (1937).
Fuller-Thomson et al., Depression and inflammatory bowel disease: findings from two nationally representative Canadian surveys, Inflamm. Bowel dis., 12(8):697-707 (2006).
George et al., A one-year comparison of vagus nerve stimulation with treatment as usual for treatment-resistant depression, Biol. Psychiatry, 58(5):364-73 (2005).
George et al., Noninvasive techniques for probing neurocircuitry and treating illness: vagus nerve stimulation (VNS), transcranial magnetic stimulation (TMS) and transcranial direct current stimulation (tDCS), Neuropsychopharmacology, 35(1):301-16 (2010).
George et al., Vagus nerve stimulation for the treatment of depression and other neuropsychiatric disorders, Exp. Rev. Neurotherapeutics, 7(1):1-12 (2007).
George et al., Vagus nerve stimulation therapy: a research update, Neurology, 59(6 Suppl 4):S56-61 (2002).

(56) References Cited

OTHER PUBLICATIONS

George et al., Vagus nerve stimulation: a new tool for brain research and therapy, Biol. Psychiatry, 47(4):287-95 (2000).
Golier et al., Low serum cholesterol level and attempted suicide, Am. J.Psychiatry, 152(3):419-23 (1995).
Goodman et al., Deep brain stimulation in psychiatry: concentrating on the road ahead, Biol. Psychiatry, 65(4):263-6 (2009).
Hart, Biological basis of the behavior of sick animals, Neurosci. Biobehav. Rev., 12(2):123-37 (1988).
Heneka et al., Locus ceruleus controls Alzheimer's disease pathology by modulating microglial functions through norepinephrine, Proc. Natl. Acad. Sci. USA, 107(13):6058-63 (2010).
Henry et al., Brain blood flow alterations induced by therapeutic vagus nerve stimulation in partial epilepsy: I. Acute effects at high and low levels of stimulation, Epilepsia, 39(9):983-90 (1998).
International Search Report and Written Opinion, corresponding International Application No. PCT/US2012/061687, dated Feb. 25, 2013.
Irnich, Georges Weiss' fundamental law of electrostimulation is 100 years old, Pacing Clin. Electrophysiol., 25(2):245-8 (2002).
Jaroch et al., Magnetic insertion system for flexible electrode implantation, J. Neurosci. Methods, 183(2):213-22 (2009).
Judd et al., A prospective 12-year study of subsyndromal and syndromal depressive symptoms in unipolar major depressive disorders, Arc. Gen. Psychiatry, 55(8):694-700 (1998).
Kanner, Depression in epilepsy: prevalence, clinical semiology, pathogenic mechanisms, and treatment, Biol. Psychiatry, 54(3):388-98 (2003).
Karege et al., Decreased serum brain-derived neurotrophic factor levels in major depressed patients, Psychiatry Res., 109(2):143-8 (2002).
Kessler et al., Lifetime and 12-month prevalence of DSM-III-R psychiatric disorders in the United States. Results from the National Comorbidity Survey, Arch. Gen. Psychiatry, 51(1):8-19 (1994).
Kessler et al., The epidemiology of major depressive disorder: results from the National Comorbidity Survey Replication (NCS-R), JAMA, 289(23):3095-105 (2003).
Kessler et al.,Lifetime prevalence and age-of-onset distributions of DSM-IV disorders in the National Comorbidity Survey Replication, Arch. Gen. Psychiatry, 62(6):593-602 (2005).
Krahl et al., Locus coeruleus lesions suppress the seizure-attenuating effects of vagus nerve stimulation, Epilepsia, 39(7):709-14 (1998).
Kroenke et al., The PHQ-9: validity of a brief depression severity measure, J. Gen. Intern. Med., 16(9):606-13 (2001).
Kunugi et al., Low serum cholesterol in suicide attempters, Biol. Psychiatry, 4192):196-200 (1997).
Kurina et al., Depression and anxiety in people with inflammatory bowel disease, J. Epidemiol. Community Health, 55(10):716-20 (2001).
Labiner et al., Vagus nerve stimulation therapy in depression and epilepsy: therapeutic parameter settings, Acta. Neurol. Scand., 115(1):23-33 (2007).
Lahmane et al., Are Wistar-Kyoto rats a genetic animal model of depression resistant to antidepressants?, Eur. J. Pharmacol., 337(2-3):115-23 (1997).
Lee et al., Depression in Alzheimer's disease: heterogeneity and related issues, Biol. Psychiatry, 54(3):353-62 (2003).
Licinio et al., The role of inflammatory mediators in the biology of major depression: central nervous system cytokines modulate the biological substrate of depressive symptoms, regulate stress-responsive systems, and contribute to neurotoxicity and neuroprotection, Mol. Psychiatry, 4(4):317-27 (1999).
Manji et al., The cellular neurobiology of depression, Nat. Med., 7(5):541-7 (2001).
Marangell et al., Neurostimulation therapies in depression: a review of new modalities, Acta. Psychiatr. Scand., 116(3):174-81 (2007).
Martin et al., Brain blood flow changes in depressed patients treated with interpersonal psychotherapy or venlafaxine hydrochloride: preliminary findings, Arch. Gen. Psychiatry, 58(7):641-8 (2001).

Mascarucci et al., Glutamate release in the nucleus tractus solitarius induced by peripheral lipopolysaccharide and interleukin-1 beta, Neuroscience, 86(4):1285-90 (1998).
McDonald et al., Prevalence, etiology, and treatment of depression in Parkinson's disease, Biol. Psychiatry, 54(3):363-75 (2003).
Mogyoros et al., Strength-duration properties of human peripheral nerve, Brain, 119(Pt.2):439-47 (1996).
Mossner et al., Consensus paper of the WFSBP Task Force on Biological Markers: biological markers in depression, World J. Biol. Psychiatry, 8(3):141-74 (2007).
Mueller et al., Recurrence after recovery from major depressive disorder during 15 years of observational follow-up, Am. J. Psychiatry, 156(7):1000-6 (1999).
Naritoku et al., Regional induction of fos immunoreactivity in the brain by anticonvulsant stimulation of the vagus nerve, Epilepsy Res., 22(1):53-62 (1995).
Nemeroff et al., Elevated concentrations of CSF corticotropin-releasing factor-like immunoreactivity in depressed patients, Science, 226(4680):1342-4 (1984).
Nemeroff et al., VNS therapy in treatment-resistant depression: clinical evidence and putative neurobiological mechanisms, Neuropsychopharmacology, 31(7):134555 (2006).
O'Brien et al., Cytokines: abnormalities in major depression and implications for pharmacological treatment, Hum. Psychopharmacol., 19(6):397-403 (2004).
O'Brien et al., Plasma cytokine profiles in depressed patients who fail to respond to selective serotonin reuptake inhibitor therapy, J. Psychiatr. Res., 41(3-4):326-31 (2007).
Paintal, Vagal sensory receptors and their reflex effects, Physiol. Rev., 53(1):159-227 (1973).
Pascual-Marqui et al., Low resolution electromagnetic tomography: a new method for localizing electrical activity in the brain, Int. J. Psychophysiol., 18(1):49-65 (1994).
Pizzagalli et al., Anterior cingulate activity as a predictor of degree of treatment response in major depression: evidence from brain electrical tomography analysis, Am. J. Psychiatry, 158(3):405-15 (2001).
Post et al., Antidepressant effects of carbamazepine, Am. J. Psychiatry, 14391):29-34 (1986).
Quan et al., Time course and localization patterns of interleukin-1beta messenger RNA expression in brain and pituitary after peripheral administration of lipopolysaccharide, Neuroscience, 83(1):281-93 (1998).
Raisman et al., High-affinity 3H-imipramine binding in platelets from untreated and treated depressed patients compared to healthy volunteers, Psychopharmacology (Berl.), 75(4):368-71 (1981).
Raison et al., Cytokines sing the blues: inflammation and the pathogenesis of depression, Trends Immunol., 27(1):24-31 (2006).
Raison et al., Depression in cancer: new developments regarding diagnosis and treatment, Biol. Psychiatry, 54(3):283-94 (2003).
Rudisch et al., Epidemiology of comorbid coronary artery disease and depression, Biol. Psychiatry, 54(3):227-40 (2003).
Rush et al., Vagus nerve stimulation (VNS) for treatment-resistant depressions: a multicenter study, Biol. Psychiatry, 47(4):276-86 (2000).
Rutecki, Anatomical, physiological, and theoretical basis for the antiepileptic effect of vagus nerve stimulation, Epilepsia, 31 Suppl 2:S1-6 (1990).
Shimizu et al., Alterations of serum levels of brain-derived neurotrophic factor (BDNF) in depressed patients with or without antidepressants, Biol. Psychiatry, 54(1):70-5 (2003).
Singer, Technology Review: Neural stimulation for autoimmune diseases (2010).
Smith et al., A Bayesian statistical analysis of behavioral facilitation associated with deep brain stimulation, J. Neurosci. Methods, 183(2)"267-76 (2009).
Solomon et al., Multiple recurrences of major depressive disorder, Am. J. Psychiatry, 157(2):229-33 (2000).
Stunkard et al., Depression and obesity, Biol. Psychiatry, 54(3):330-7 (2003).
Sun et al., Responsive cortical stimulation for the treatment of epilepsy, Neurotherapeutics, 5(1):68-74 (2008).

(56) References Cited

OTHER PUBLICATIONS

Tracey, Physiology and immunology of the cholinergic antiinflammatory pathway, J. Clin. Invest., 117(2):289-96 (2007).
Tracey, Reflex control of immunity, Nat. Rev. Immunol., 9(6):418-28 (2009).
Tracey, The inflammatory reflex, Nature, 420(6917):853-9 (2002).
Tung et al., Using finite state automata to produce self-optimizaion and self-control., IEEE Trans. Parallel Distributed Systems, 7(4):439-48 (1996).
Vitkovic et al., Cytokine signals propagate through the brain, Mol. Psychiatry, 5(6):604-15 (2000).
Walker et al., Regulation of limbic motor seizures by GABA and glutamate transmission in nucleus tractus solitarius, Epilepsia, 40(8):1051-7 (1999).
Ward et al., Characterizing the antiepileptic effects of vagus nerve stimulation by quanityfing local field potential and neurotransmitter dynamics in vagus nerve afferents, Presented at the 2010 Society for Neuroscience Conference in San Diego, California (2010).
Ward et al., Evolving refractory major depressive disorder diagnostic and treatment paradigms: toward closed-loop therapeutics, Front. Neuroeng., 3:7 (2010).
Ward et al., Toward a comparison of microelectrodes for acute and chronic recordings, Brain Res., 1282:183-200 (2009).
Wells et al., The functioning and well-being of depressed patients. Results from the Medical Outcomes Study, JAMA, 262(7):914-9 (1989).
Wong et al., Closed-loop control of cellular functions using combinatory drugs guided by a stochastic search algorithm, Proc. Natl. Acad. Sci. USA, 105(13):5105-10 (2008).
Woodbury et al., Effects of vagal stimulation on experimentally induced seizures in rats, Epilepsia, 31 Suppl 2:S7-19 (1990).
European Search Report, corresponding European Application No. 12842909.9, dated Apr. 20, 2015.

* cited by examiner

METHOD AND APPARATUS FOR CLOSED-LOOP CONTROL OF NERVE ACTIVATION

TECHNICAL FIELD

The present disclosure generally relates to physiological nervous systems and particularly to devices and methods to measure and manipulate signals associated with these systems.

BACKGROUND

The vagal nerves are the largest and most evolved nerves in the human body. They perform mostly sensory and parasympathetic functions within the autonomic nervous system, using acetylcholine (ACh) as the sole neurotransmitter. The left vagus nerve is a mixed nerve with ~100,000 axons, of which an estimated 65-80% are visceral afferent sensory fibers with sensory receptors located within the aorta, gastrointestinal tract, heart, lungs and esophagus, among others. See J. O. Foley, and F. DuBois, "Quantitative studies of the vagus nerve in the cat. I. The ratio of sensory to motor fibers," *J Comp Neurol*, vol. 67, pp. 49-97, 1937; and P. Rutecki, "Anatomical, physiological, and theoretical basis for the antiepileptic effect of vagus nerve stimulation," *Epilepsia*, vol. 31, pp. S1-S6, 1990. Vagal efferents are myelinated and originate primarily from the dorsal motor nucleus (DMN) of the vagus. See P. Rutecki, "Anatomical, physiological, and theoretical basis for the antiepileptic effect of vagus nerve stimulation," *Epilepsia*, vol. 31, pp. S1-S6, 1990. The afferent fibers project primarily to the nucleus tractus solitarius (NTS), where diffuse projections convey the visceral (and some somatic) sensory information throughout the central nervous system (CNS), including areas in the limbic system and cortex that regulate emotion. See U. N. Das, "Vagus nerve stimulation, depression, and inflammation," *Neuropsychopharmacology*, vol. 32, pp. 2053-2054, 2007. Many of the afferent fibers participate in autonomic reflexes involved in maintaining homeostasis and have myelinated projections from the nodose ganglion to the NTS, DMN, area postrema, nucleus cunneatus and the medial reticular formation (The nodose ganglion comprises the somata of unipolar sensory neurons, with unmyelinated projections inferior to and myelinated projections superior to the nodose ganglion, respectively). See A. S. Paintal, "Vagal sensory receptors and their reflex effects," *Physiol Rev*, vol. 53, pp. 159-227, 1973. The NTS directly communicates with the reticular formation, area postrema and DMN; it also indirectly communicates with the thalamus, hypothalamus, amygdala, cingulate gyms, and orbitofrontal cortex via the locus coeruleus (LC) and parabrachial nucleus (PB). See M. S. George, and G. Aston-Jones, "Noninvasive techniques for probing neurocircuitry and treating illness: Vagus nerve stimulation (VNS), transcranial magnetic stimulation (TMS) and transcranial direct cunent stimulation (tDCS)," *Neuropsychopharmacology REVIEWS*, vol. 35, pp. 301-316, 2010; and M. S. George, Z. Nahas, J. J. Borckardt et al., "Vagus nerve stimulation for the treatment of depression and other neuropsychiatric disorders," *Expert Rev. Neurotherapeutics*, vol. 7, no. 1, pp. 1-12, 2007.

FIGS. 7A through 7C depict various implementations of VNS devices with associated implant locations according to prior art. FIG. 7A depicts a VNS device housing and electrode implant location. See M. S. George, H. A. Sackeim, A. J. Rush et al., "Vagus nerve stimulation: A new tool for brain research and therapy," *Biol Psychiatry*, vol. 47, pp. 287-295, 2000. FIG. 7B depicts a cross-section of a human brainstem showing the primary sites of vagal input (the NTS, or "solitary tract") and output (the DMN, or "dorsal nuc. of X"). See Id. Referring to FIG. 7C, a summary of NTS efferent projections that impart diffuse, nerve activation level and rate-dependent effects on CNS function is depicted. See M. S. George, Z. Nahas, J. J. Borckardt et al., "Vagus nerve stimulation for the treatment of depression and other neuropsychiatfic disorders," *Expert Rev. Neurotherapeutics*, vol. 7, no. 1, pp. 1-12, 2007. The NTS projects to the LC, where effective vagus nerve stimulation is believed to excite noradrenergic neurons, resulting in norepinephfine release in several structures of the limbic system and frontal lobe implicated in temporal lobe epilepsy (TLE) and major depressive disorder (MDD). This has been found to suppress inflammation in the CNS associated with Alzheimer's disease. See M. T. Heneka, F. Nadfigny, T. Regen et al., "Locus ceruleus controls Alzheimer's disease pathology by modulating microglial functions through norepinephfine," *PNAS*, vol. 107, no. 13, pp. 6058-6063, 2010.

Vagus nerve stimulation (VNS) has been available since 1994 in Europe and 1997 in the United States as a therapy for treatment-resistant partial onset seizures, where it has helped tens of thousands of patients with drug-resistant TLE experience significant seizure rate reductions. The prospect of using VNS as an alternative therapy for refractory MDD originated from unexpected patient-reported mood improvements observed in the NeuroCybernetic Prosthesis System trials in the 1990s and the off-label uses of specific seizure medications for stabilizing mood disorders. See M. S. George, H. A. Sackeim, A. J. Rush et al., "Vagus nerve stimulation: A new tool for brain research and therapy," *Biol Psychiatry*, vol. 47, pp. 287-295, 2000; E. BenMenachem, R. Manon-Espaillat, R. Ristanovic et al., "Vagus nerve stimulation for treatment of partial seizures: 1. A controlled study of effects on seizures," *Epilepsia*, vol. 35, no. 3, pp. 616-626, 1994; J. C. Ballenger, and R. M. Post, "Carbamazepine in manic-depressive illness: a new treatment," *Am J Psychiatry*, vol. 137, pp. 782-790, 1980; and R. M. Post, T. W. Uhde, P. P. Roy-Byrne et al., "Antidepressant effects of carbamazepine," *Am J Psychiatry*, vol. 143, pp. 29-34, 1986. Several treatment-resistant epileptic patients implanted with the VNS device reported significant mood elevations that researchers could not solely attribute to seizure frequency reduction. Additional positron-emission tomography (PET) studies showed that VNS reduced cingulate activity, the same effect seen from many successful antidepressant therapies, and altered blood flow and metabolism in limbic structures. See M. S. George, H. A. Sackeim, A. J. Rush et al., "Vagus nerve stimulation: A new tool for brain research and therapy," *Biol Psychiatry*, vol. 47, pp. 287-295, 2000; and T. R. Henry, R. A. E. Bakay, J. R. Votaw et al., "Brain blood flow alterations induced by therapeutic vagus nerve stimulation in partial epilepsy: I. Acute effects at high and low levels of stimulation," *Epilepsia*, vol. 39, no. 9, pp. 983-990, 1998. Researchers have also shown that long-term VNS, for durations of 10 weeks or greater, produces widespread inhibitory effects in the CNS. Specifically, Lazzaro and colleagues applied transcranial magnetic stimulation (TMS) over the motor cortex and demonstrated that long-term VNS produced significant decreases in motor cortical excitability in epileptic patients (in 2007, this experiment was repeated in VNS device recipients with MDD, where the same reductions in cortical excitability were observed). See V. Di Lazzaro, A. Oliviera, F. Pilato et al., "Effects of vagus nerve stimulation on cortical excitability in epileptic patients," *Neurology*, vol. 62, no. 12, pp. 2310-2312, 2004;

and M. Bajbouj, J. Gallinat, U. E. Lang et al., "Motor cortex excitability after vagus nerve stimulation in major depression," *J Clin Psychopharmacol.*, vol. 27, no. 2, pp. 156-159, 2007. Other investigations indicated that neurotransmitter levels are altered as a result of VNS. See E. Ben-Menachem, A. Hamberger, T. Hedner et al., "Effects of vagus nerve stimulation on amino acids and other metabolites in the CSF of patients with partial seizures," *Epilepsy Research*, vol. 20, no. 3, pp. 221-227, 1995; and S. E. Krahl, K. B. Clark, D. C. Smith et al., "Locus coeruleus lesions suppress the seizure-attenuating effects of vagus nerve stimulation," *Epilepsia*, vol. 39, no. 7, pp. 709-714, 1998. Due to this observation and the unexpected reports of mood improvement, the first VNS device for the treatment of unipolar refractory MDD was implanted by Rush and colleagues in 1998. See M. S. George, H. A. Sackeim, A. J. Rush et al., "Vagus nerve stimulation: A new tool for brain research and therapy," *Biol Psychiatry*, vol. 47, pp. 287-295, 2000; and A. J. Rush, M. S. George, H. A. Sackeim et al., "Vagus Nerve Stimulation (VNS) for treatment-resistant depressions: A multicenter study," *Biol Psychiatry*, vol. 47, pp. 276-286, 2000. Response rates (i.e., A patient is a responder if a standardized depression rating scale score is reduced by >50% in response to the therapy) of 27-40% were observed after at least 8 weeks of VNS therapy; robust and durable antidepressant responses are seen after 12 or more months of VNS therapy. See M. S. George, Z. Nahas, D. E. Bohning et al., "Vagus nerve stimulation therapy: A research update," *Neurology*, vol. 59, no. Suppl. 4, pp. S56-S61, 2002; and M. S. George, A. J. Rush, L. B. Marangell et al., "A one-year companson of vagus nerve stimulation with treatment as usual for treatment-resistant depression," *Biol Psychiatry*, vol. 58, pp. 364-373, 2005. The FDA approved VNS for refractory MDD in July 2005. See M. S. George, H. A. Sackeim, A. J. Rush et al., "Vagus nerve stimulation: A new tool for brain research and therapy," *Biol Psychiatry*, vol. 47, pp. 287-295, 2000; C. B. Nemeroff, H. S. Mayberg, S. E. Krahl et al., "VNS therapy in treatment-resistant depression: Clinical evidence and putative neurobiological mechanisms," *Neuropsychopharmacology*, vol. 31, pp. 1345-1355, 2006.

The VNS device implant procedure is rather straightforward. Under general anesthesia, the VNS device housing is surgically implanted in the left chest wall. A projecting stimulation lead with an attached helical electrode is then wrapped around the left cervical vagus nerve and secured to surrounding tissue. The device is externally activated and programmed using a wand like device placed over the left chest wall. Stimulation is intermittent and commonly programmed for 30 s of monophasic, constant-current stimulation every 5 min. However, individual parameters are adjusted on a patient-to-patient basis in order to achieve maximal therapeutic efficacy with minimal side effects. See L. B. Marangell, M. Martinez, R. A. Jurdi et al., "Neurostimulation therapies in depression: A review of new modalities," *Acta Psychiatrica Scandinavica*, vol. 116, pp. 174-181, 2007. Common side effects, such as dyspnea, cough and hoarseness, are dependent on the intensity of stimulation; they have been reported to diminish with time. To minimize patient discomfort, the stimulus intensity is typically slowly increased over 2 week intervals until a balance is found between the maximum stimulus intensity and the patients' willingness to accept any side effects. See M. S. George, and G. Aston-Jones, "Noninvasive techniques for probing neurocircuitry and treating illness: Vagus nerve stimulation (VNS), transcranial magnetic stimulation (TMS) and transcranial direct cunent stimulation (tDCS)," *Neuropsychopharmacology REVIEWS*, vol. 35, pp. 301-316, 2010. The current method of parameter optimization can be complex and time consuming for the patient and physician. Table 1 summarizes a protocol for stimulus parameter adjustments after implantation. Table 2 summarizes available device settings and common variations used in treating depression and epilepsy. See D. M. Labiner, and G. L. Ahern, "Vagus nerve stimulation therapy in depression and epilepsy: therapeutic parameter settings," *Acta Psychiatrica Scandinavica*, vol. 115, pp. 23-33, 2007.

TABLE 1

Suggested stimulus parameter adjustment protocol
(Labiner and Ahern, 2007)

| To increase efficacy | To manage side effects |
|---|---|
| 1. ≥2 weeks after implant, increase output current by 0.25-0.5 mA at 2-week intervals to maximum tolerated level, typically 1.0-2.0 mA. | 1. Reduce output current |
| | 2. Reduce pulse width |
| | 3. Reduce frequency |
| | 4. Reduce ON time |
| 2. If no response after 1-3 months at maximum tolerated output current, gradually increase duty cycle (increase ON time, decrease OFF time) | |

TABLE 2

Overview of available VNS stimulus parameter settings (Labiner and Ahern, 2007)

| Stimulation parameters | Programmable range | Programming steps | Recommended initial values | Typical target values |
|---|---|---|---|---|
| Output current | 0-35 mA | 0.25 mA | 0.25 mA | 1.0-2 mA |
| Frequency | 1-30 Hz[1] | 1, 2, 5, 10, 15, 20, 25, 30 Hz | 20 Hz[2] 30 Hz[3] | 20-30 Hz |
| Pulse width | 130-1000 μs | 130, 250, 500, 750, 1000 μs | 250-500 μs | 250-500 μs |
| Duty cycle | 10-100%[4] | Function of signal ON, OFF times | 10% | 10% |
| Signal ON time | 7-60 s | 7, 14, 21, 30, 60 s | 30 s | 30 s |
| Signal OFF time | 0.2-180 min[5] | 5-60 min, 5-min steps 50-180 min, 30-min steps | 5 min | 5 min |

[1]Values below 5 Hz should be avoided.
[2]In depression.
[3]In epilepsy.
[4]Duty cycles greater than 50% have resulted in nerve damage in laboratory animals [26].
[5]Setting OFF time to 0.0 min turns off time pulse generator.

Many of the VNS studies published to date conclude that VNS imparts its antiepileptic and antidepressive effects through activation of vagal afferent fibers. This is a logical conclusion, because: 1) the device is intended to treat neuronal network-level disorders in the CNS, 2) vagal afferent fibers primarily project to the NTS and onward to the LC, where a chemical lesion was shown to significantly attenuate VNS-mediated anticonvulsive activity, and 3) evoked potentials from VNS have been repeatedly observed in neural recording/imaging studies. See S. E. Krahl, K. B. Clark, D. C. Smith et al., "Locus coeruleus lesions suppress the seizure-attenuating effects of vagus nerve stimulation," *Epilepsia*, vol. 39, no. 7, pp. 709-714, 1998. However, the conclusion that VNS works by activating unmyelinated C fibers of the vagus nerve is debated, because 1) destruction of C fibers does not destroy the antiepileptic effect of VNS and 2) stimuli found to be effective in epilepsy are of insufficient strength to activate the unmyelinated, afferent C fibers. See M. S. George, Z. Nahas, D. E. Bohning et al., "Vagus nerve stimulation therapy: A research update," *Neurology*, vol. 59, no. Suppl. 4, pp. S56-S61, 2002; D. M. Woodbury, and J. W. Woodbury, "Effects of vagal stimulation on experimentally induced seizures in rats," *Epilepsia*, vol. 31, no. Suppl. 2, pp. S7-S19, 1990; and M. S. Evans, S. Verma-Ahuja, D. K. Naritoku et al., "Intraoperative human vagus nerve compound action potentials," *Acta Psychiatrica Scandinavica*, vol. 110, pp. 232-238, 2004.

Research on communication pathways between the immune, endocrine and central nervous systems in the past several decades suggests alternative, under-recognized pathways through which VNS may impart an antidepressive effect. A series of discoveries by Dr. Kevin J. Tracey and colleagues in the last decade led his startup company, SetPoint Medical, to begin clinical trials of VNS for the treatment of inflammation associated with autoimmune disorders such as rheumatoid arthritis (RA) and inflammatory bowel disease (MD). See E. Singer, "Technology Review: Neural Stimulation for Autoimmune Diseases," *A startup is developing an implanted stimulator to treat such illnesses as arthritis and inflammatory bowel disease,* 2010]. The work that led to the discovery of VNS' potential in treating inflammatory disorders was a demonstration that VNS prevents sepsis by inhibiting macrophage activation and reducing proinflammatory cytokine (PIC) production. See L. V. Borovikova, S. Ivanova, M. Zhang et al., "Vagus nerve stimulation attenuates the systemic inflammatory response to endotoxin," *Letters to Nature*, vol. 405, pp. 458-462, 2000. It was found that VNS modulated a previously unrecognized communication pathway between the immune system and CNS, named the cholinergic anti-inflammatory reflex. See K. J. Tracey, "The inflammatory reflex," *NATURE, vol.* 420, pp. 853-859, 2002; K. J. Tracey, "Physiology and immunology of the cholinergic anti-inflammatory pathway," *The Journal of Clinical Investigation*, vol. 117, no. 2, pp. 289-296, 2007; and K. J. Tracey, "Reflex control of immunity," *Nature Review Immunology*, vol. 9, pp. 418-428, 2009. The afferent arm of the reflex senses PICs and/or pathogenic antigens at the site of injury or infection and relays the information to the NTS. Although the precise relationship is still unknown, the NTS signals the DMN of the vagus in proportion to the level of sensory input into the NTS. The DMN then reflexively increases efferent output to vagal nerve innervated structures, where ACh is released. See Id. Mainly through vagal projections to the spleen, ACh imparts a graded anti-inflammatory effect by binding to the a7 nicotinic acetylcholine receptors (a7nAChR) on PIC-producing immune cells (e.g., macrophages). When ACh binds to the a7nAChR, PIC production and release is suppressed. Therefore, VNS-mediated modulation of the cholinergic anti-inflammatory reflex effectively suppresses the over-active immune system in patients with autoimmune inflammatory disorders. The cholinergic anti-inflammatory reflex is a significant discovery, because it imparts tonic, rapid and direct neural control over immune system activity. See E. Singer, "Technology Review: Neural Stimulation for Autoimmune Diseases," *A startup is developing an implanted stimulator to treat such illnesses as arthritis and inflammatory bowel disease,* 2010; L. V. Borovikova, S. Ivanova, M. Zhang et al., "Vagus nerve stimulation attenuates the systemic inflammatory response to endotoxin," *Letters to Nature*, vol. 405, pp. 458-462, 2000; and K. J. Tracey, "Reflex control of immunity," *Nature Review Immunology*, vol. 9, pp. 418-428, 2009. Due to its accessibility in the vagus nerve, any abnormality in its function can theoretically be treated with VNS. However, as with VNS for TLE and MDD, the interplay between the applied stimulus parameters and associated effects must be better understood for VNS to realize its full therapeutic potential.

Rheumatoid arthritis and MD (e.g., Crohn's disease and ulcerative colitis) are associated with high rates of comorbid depression. See E. Fuller-Thomson, and J. Sulman, "Depression and inflammatory bowel disease: Findings from two nationally representative Canadian surveys," *Inflamm Bowel Dis*, vol. 12, pp. 697-707, 2006; and L. M. Kurina, M. J. Goldacre, D. Yeates et al., "Depression and anxiety in people with inflammatory bowel disease," *J Epidemiol Community Health*, vol. 55, pp. 716-720, 2001. It is not known whether depression precedes the disorders or results from the effects of the disorders, but depressed patients with MD typically experience a depressive episode within a year of their MD diagnosis. See Id. Table 3 provides an overview of other chronic medical conditions associated with high rates of comorbid depression. See D. L. Evans, D. S. Chamey, L. Lewis et al., "Mood disorders in the medically ill: Scientific review and recommendations," *Biol Psychiatry*, vol. 58, pp. 175-189, 2005. A key factor common to many, if not all of the conditions, is inflammation. It is proposed that an excessive or prolonged inflammatory response, due to an autoimmune disease, persistent/recurrent infection, or injury, can lead to a misdiagnosis of refractory MDD. These individuals may not respond well to conventional antidepressant therapy, because the drugs are not targeting the source of the symptoms: Cytokine-induced depression (i.e., "sickness behavior"). See C. L. Raison, and A. H. Miller, "Depression in cancer: New developments regarding diagnosis and treatment," *Biol Psychiatry*, vol. 54, pp. 283-294, 2003. The depressive symptoms may be alleviated in these individuals by reducing circulating levels of PICs, which are ultimately responsible for many of the depressive symptoms due to their effects on key regions of the brain that control emotion, mood and motivation. See G. Cizza, A. H. Marques, F. Eskandan et al., "Elevated neuroimmune biomarkers in sweat patches and plasma of premenopausal women with major depressive disorder in remission: The POWER study," *Biol Psychiatry*, vol. 64, pp. 907-911, 2008; and Y. Dowlati, N. Hermann, W. Swardfager et al., "A meta-analysis of cytokines in major depression," *Biol Psychiatry*, vol. 67, pp. 446-457, 2010. Others have worked out many of the neural-immune communication pathways and their relationship to depression. Tracey and colleagues are exploring VNS for autoimmune inflammatory disorders. Since VNS reduces inflammation in inflammatory disorders associated with high rates of comorbid depression (e.g., RA and MD), VNS-mediated modulation of the cholinergic anti-inflammatory reflex may be an important component of the therapeutic mechanisms of VNS in refractory MDD patients. A review of the literature identified one other individual who has considered the link between modulation of the cholinergic anti-inflammatory reflex, inflammation and depression: Undurti N. Das, a specialist in metabolic syndrome pathophysiology. See U. N. Das, "Vagus nerve stimulation, depression, and inflammation," *Neuropsychopharmacology*, vol. 32, pp. 2053-2054, 2007. However, he has not fully developed the hypothesis or attempted to test it.

TABLE 3

Comorbid depression in chronic illness (Adapted from Evans et al.)

| Chronic Illness | Depression Prevalence Rate (%) | Reference |
|---|---|---|
| General Population (no known illness) | 10.3 | Kessler et al., 1994 |
| Parkinson's Disease | 4-75 | McDonald et al., 2003 |
| Epilepsy (Recurrent/Refractory) | 20-55 | Kanner, 2003 |
| Pain | 30-54 | Campbell et al., 2003 |
| Rheumatoid Arthritis | 42 | Bruce, 2008 |
| Alzheimer's Disease | 30-50 | Lee and Lyketsos, 2003 |
| Obesity | 20-30 | Stunkard et al., 2003 |
| Cancer | 22-29 | Raison and Miller, 2003 |
| Cardiac Disease | 17-27 | Rudisch and Nemeroff, 2003 |

See R. C. Kessler, K. A. McGonagle, S. Zhao et al., "Lifetime and 12-month prevalence of DSM-III-R psychiatric disorders in the United States," Arch Gen Psychiatry, vol. 51, pp. 8-19, 1994; W. M. McDonald, I. H. Richard, and M. R. DeLong, "The prevalence, etiology and treatment of depression in Parkinson's disease," Biol Psychiatry, vol. 54, pp. 363-375, 2003; A. M. Kanner, "Depression in epilepsy: Prevalence, clinical semiology, pathogenic mechanisms, and treatment," Biol Psychiatry, vol. 54, pp. 388-398, 2003; L. C. Campbell, D. J. Clauw, and F. J. Keefe, "Persistent pain and depression: A biopsychosocial perspective," Biol Psychiatry, vol. 54, pp. 399-409, 2003; T. 0. Bruce, "Comorbid depression in rheumatoid arthritis: Pathophysiology and clinical implications," Curr Psychiatry Rep., vol. 10, no. 3, pp. 258-264, 2008; H. B. Lee, and C. G. Lyketsos, "Depression in Alzheimer's disease: Heterogeneity and related issues," Biol Psychiatry, vol. 54, pp. 353-362, 2003; A. J. Stunkard, M. S. Faith, and K. C. Allison, "Depression and obesity," Biol Psychiatry, vol. 54, pp. 330-337, 2003; and B. Rudisch, and C. B. Nemeroff, "Epidemiology of comorbid coronary artery disease and depression," Biol Psychiatry, vol. 54, pp. 227, 2003.

In addition, depression is among the top predictors of mortality and substandard daily functioning in North America, second only to cardiovascular disorders. See K. B. Wells, A. Stewart, R. D. Hays et al., "The functioning and well-being of depressed patients: Results from the medical outcomes study," *JAMA*, vol. 262, pp. 914-919, 1989. Due to conventional symptom-based classification schemes and an incomplete understanding of the disorder, the term "depression" is used to describe a broad set of disparate pathologies sharing a common set of symptoms—pathologies that manifest as abnormal control and expression of mood and emotion. See R. J. Davidson, D. Pizzagalli, J. B. Nitschke et al., "Depression: Perspectives from affective neuroscience," *Annu. Rev. Psychol.*, vol. 53, pp. 545-574, 2002. Depressed individuals may experience a dispirited mood, a lowered sense of enthusiasm or enjoyment with routine tasks (i.e., anhedonia), a disrupted sleep schedule, altered behavior, appetite, or weight, a change in the speed of muscle movements, a decreased energy level, an inability to focus, thoughts of worthlessness or guilt, and thoughts of death or suicide over an extended period of time. See "American Psychiatric Association: *Diagnostic and Statistical Manual of Mental Disorders*, Text Revision," Fourth ed., Washington, D.C.: R. R. Donnelly & Sons Company, 2000; and K. Kroenke, R. L. Spitzer, and J. B. W. Williams, "The PHQ-9: Validity of a brief depression severity measure," *J Gen Intern Med*, vol. 16, pp. 606-613, 2001. Current treatment measures do not effectively control symptoms in most depressed patients, especially the estimated 4 million Americans with the severe treatment-resistant subtype known as refractory major depressive disorder. See Cyberonics, "About treatment resistant depression," VNS Therapy, Cyberonics, ed., 2007; and R. C. Kessler, P. Berglund, O. Demler et al., "Lifetime prevalance and age-of-onset distributions of DSM-IV disorders in the National Comorbidity Survey Replication," *Arch Gen Psychiatry*, vol. 62, no. 6, pp. 593-602, 2005.

Refractory MDD is characterized by recurrent, long-lasting cycles of severe, often suicidal depressive episodes that do not remit using multiple types of antidepressant therapies. A depressive episode persists for up to a year, significantly impairing the health and daily activities of the afflicted. See L. L. Judd, H. S. Akiskal, J. D. Maser et al., "A prospective 12-year study of subsyndromal and syndromal depressive symptoms in unipolar major depressive disorders," *Arch Gen Psychiatry*, vol. 55, pp. 694-700, 1998; and H. K. Manji, W. C. Drevets, and D. S. Charney, "The cellular neurobiology of depression," *Nature Medicine*, vol. 7, no. 5, pp. 541-547, 2001. In fact, the net loss of productivity stemming from the disorder costs the United States an estimated 83 billion dollars each year. See J. C. Coyne, S. Fechner-Bates, and T. L. Schwenk, "Prevalence, nature, and comorbidity of depressive disorders in primary care," *Gen Hosp Psychiatry*, vol. 16, pp. 267, 1994. Even with the best FDA-approved antidepressant treatments, the majority of MDD patients will inevitably suffer from multiple depressive episodes during their lifetime. See R. C. Kessler, P. Berglund, O. Demler et al., "The epidemiology of major depressive disorder: Results from the National Comorbidity Survey Replication (NCS-R)," *JAMA*, vol. 289, no. 23, pp. 3095-3105, 2003; and T. I. Mueller, A. C. Leon, M. B. Keller et al., "Recurrence after recovery from major depressive disorder during 15 years of observational follow-up," *Am J Psychiatry*, vol. 156, no. 7, pp. 1000-1006, 1999. To make matters worse, each recurrent depressive episode puts the patient at a 16% increased risk for developing an additional depressive episode during their lifetime, often presenting with more severe symptoms than previous episodes. See D. A. Solomon, M. B. Keller, A. C. Leon et al., "Multiple Recurrences of Major Depressive Disorder," *Am J Psychiatry*, vol. 157, no. 2, pp. 229-233, 2000.

Stimulation-based technologies, designed to electrically or chemically modulate abnormal neural activity, are emerging as potential therapeutic options for refractory MDD patients. However, the expected treatment efficacies of these technologies, as with all antidepressant treatments, are burdened by an incomplete understanding of the pathophysiology of depressive disorders and a lack of reproducible and quantifiable biological markers (i.e., biomarkers) of depressed states (Antidepressant treatment response is still subjectively evaluated using patient-reported symptom relief, effectively ignoring the prospect of using objectively quantified, depression-linked biomarker levels to quantify antidepressant responses and to optimize treatment). With modern research tools, additional structural, functional, and genetic abnormalities associated with depression are discovered each year. Concomitantly, several quantifiable genetic, biochemical, and bioelectric diagnostic markers of depression are emerging. Similar discoveries in the epilepsy research field sparked interest in closed-loop neuroprostheses, where biological indicators of an impending seizure are used to determine the time at which an electrical or chemical stimulus must be applied to stop a seizure. See D. Dumitriu, K. Collins, R. Alterman et al., "Neurostimulatory therapeutics in management of treatment-resistant depression with focus on deep brain stimulation," *Mount Sinai Journal of Medicine*, vol. 75, pp. 263-275, 2008. This process, known as responsive neurostimulation, is unique to closed-loop devices. It is intended to replace continuous or periodic open-loop stimulation designs so that tailored therapy, based on quantifiable symptom-linked biomarker abnormalities, is provided in a dose dependent manner only when it is necessary. See W. K. Goodman, and T. R. Insel, "Deep brain stimulation in psychiatry: Concentrating on the road ahead," *Biol Psychiatry*, vol. 65, pp. 263-266, 2009; and F. T. Sun, M. J. Morrell, and R. E. Wharen, "Responsive cortical stimulation for the treatment of epilepsy," *Neurotherapeutics*, vol. 5, no. 1, pp. 68-74, 2008.

Therefore, there is a need for a system and method to improve the efficacy of existing VNS therapy in patients suffering from refractory MDD with additional benefits for patients with refractory TLE through a system implementing closed-loop stimulus parameter optimization algorithms

SUMMARY

The significance for the present disclosure is highlighted by a system executing an algorithm to autonomously predict a plurality of electrical pulse durations and amplitudes that activate a predefined proportion of distinct nerve fiber groups, wherein the algorithm predicts electrical stimulus parameters that can activate 0-100% of the nerve fibers groups selectively according to a patient's characteristics and proportional to therapeutic outcomes as determined by experimental data. The system is further configured to input experimental third-party data and calibrate the algorithm to obtain a high efficacy from a patient without invasive neurosurgery by a) identifying a mechanism of action associated with vagus nerve stimulation (VNS) suppression of seizure activity; b) correlating the mechanism with a specific biomarker; c) correlating vagus nerve fiber recruitment with biomarker levels in a test animal; and d) design an automated "closed-loop" VNS stimulator that affixes at the same therapeutic efficacy without requiring biomarker sensing based only on recruitment patterns recorded from the vagus nerve rostral to the stimulation site to thereby identify the optimal stimulation parameters as a function of specific biomarkers for seizure suppression in a small patient or animal population, wherein correlating biomarker levels with recruitment patterns in the nerve provides the same therapeutic efficacy to patients using a single additional electrode on the vagus nerve, and without a cortically invasive device.

DETAILED DESCRIPTION

Figure 1:
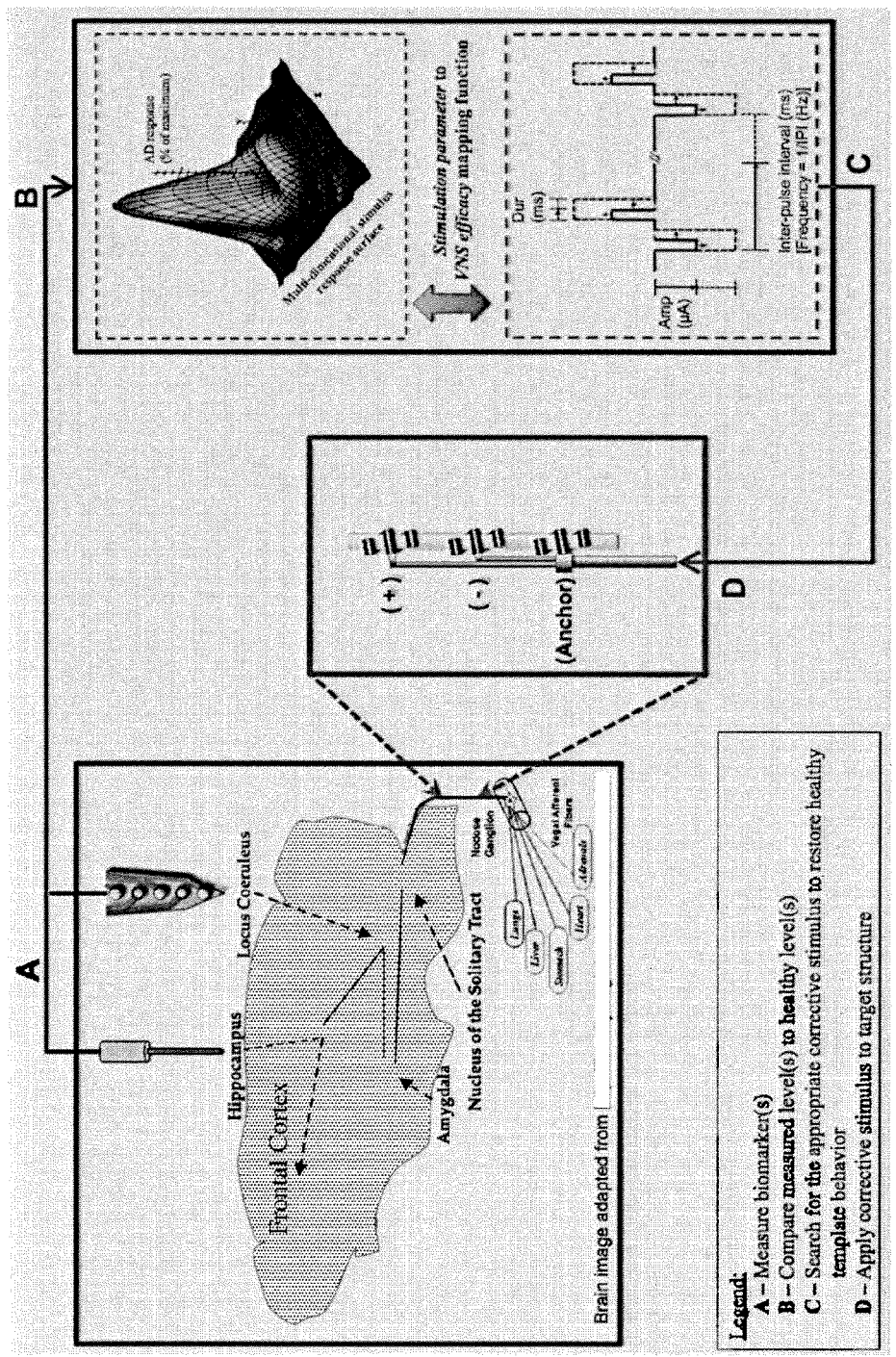
FIG. 1 is a schematic of a generic model for closed-loop control of Vagus nerve stimulation (VNS) efficacy (in rat), in which sets of disorder- or symptom-linked biomarkers are used as control points for real-time stimulus parameter optimization.

For the purpose of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel system and method for treating neurological disorders has been developed. The system improves the efficacy of existing Vagus nerve stimulation (VNS) therapy, such as for patients suffering from refractory major depressive disorder (MDD) with additional implications for patients with refractory temporal lobe epilepsy (TLE). The efficacy of VNS therapy can be enhanced through the design and implementation of closed-loop stimulus parameter optimization algorithms, which use symptom- or disorder-linked biomarkers as control points for maximizing therapeutic outcomes.

Referring to FIG. 1, a schematic of a generic model for closed-loop control of VNS efficacy (in rat), in which sets of disorder- or symptom-linked biomarkers are used as control points for real-time stimulus parameter optimization is depicted. See M. P. Ward, and P. P. Irazoqui, "Evolving refractory major depressive disorder diagnostic and treatment paradigms: toward closed-loop therapeutics," *Frontiers in Neuroengineering*, vol. 3, no. 7, pp. 1-15, 2010; and M. P. Ward, J. L. Rickus, and P. P. Irazoqui, "Characterizing the antiepileptic effects of vagus nerve stimulation by quantifying local field potential and neurotransmitter dynamics in vagus nerve afferents," Presented at the 2010 *Society for Neuroscience Conference in San Diego*, Calif., 657.17, Purdue University Center for Implantable Devices, 2010. In FIG. 1 the following abbreviations are used: AD—antidepressive; Dur—duration; Amp—amplitude.

Figure 2:
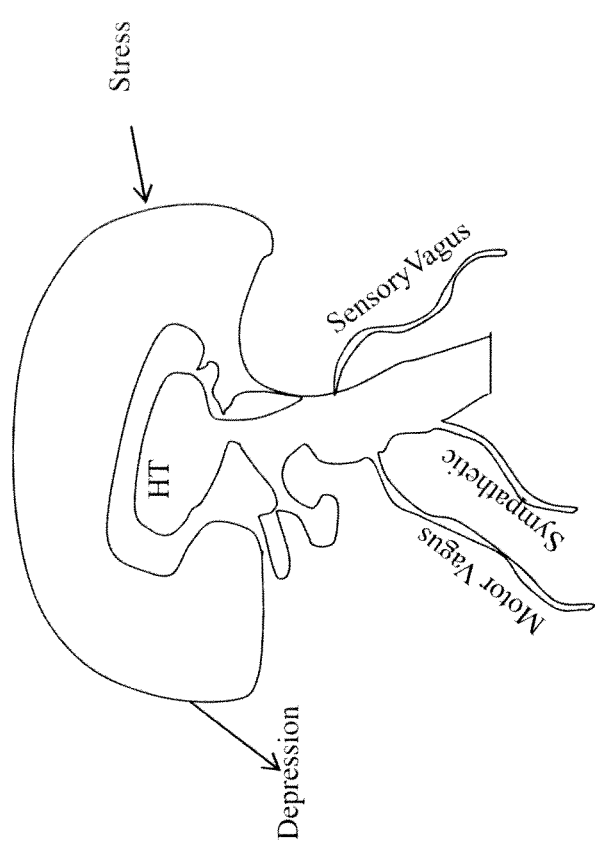
FIG. 2 is a diagram picture of vagal afferent and efferent pathways in relation to depression and immunity FIG. 3 (left hand side) represents graphs showing 3 SD curves in hyperbolic and linear form where each curve represents the threshold for 30, 60 and 90% maximal activation, respectively; and the right side is a plot of rheobase current versus % maximal activation (using data from Mogyoros et al.).

Referring to FIG. 2 a schematic diagram of vagal afferent and efferent pathways in relation to depression and immunity are depicted. One should note the dynamic interactions of innate and adaptive immunity, glucocorticoids and the cholinergic anti-inflammatory reflex. In addition, one should note the opposing effects of acetylcholine (Ach), norepinephrine and glucocorticoids on pro-inflammatory cytokine production. See C. L. Raison, L. Capuron, and A. H. Miller, "Cytokines sing the blues: Inflammation and the pathogenesis of depression," *TRENDS in Immunology*, vol. 27, no. 1, pp. 24-31, 2006.

Most of the VNS literature published since the 1980s focuses on the mechanisms of VNS in refractory TLE, with little regard for the mechanisms of VNS in refractory MDD. Since VNS is approved for treating refractory MDD and TLE, and since the observed therapeutic effect in both disorders implies one or more common therapeutic mechanisms, it is believed that unique insights into both disorders can be gained by simultaneously studying the effects of VNS in refractory MDD and TLE. However, given the relative neglect that VNS for refractory MDD has experienced since it was first applied in humans, one focus point of the present disclosure is on improving VNS therapy for patients with refractory MDD.

Since no robust biomarkers of MDD have been identified to date, a first step according to the present disclosure is to identify likely candidates. This can be accomplished through a comprehensive literature survey published by the Center for Implantable Devices in 2010 (Table 4). See M. P. Ward, and P. P. Irazoqui, "Evolving refractory major depressive disorder diagnostic and treatment paradigms: toward closed-loop therapeutics," *Frontiers in Neuroengineering*, vol. 3, no. 7, pp. 1-15, 2010. Due to the heterogeneous nature of the disorder, which appears to wise from a heterogeneous set of environmental and genetic factors, and the mixed set of physical and psychological symptoms that may or may not be present in all MDD patients, it is likely that no universal biomarker of MDD exists as the disorder is currently defined. However, robust biomarkers may exist for related symptoms in specific subtypes of the disorder that share common symptom profiles and/or develop through similar circumstances. Toward this end, a common reference is needed for quantifying candidate symptom-linked biomarker responses to VNS. The current practice of reporting applied stimulus parameters and subjectively-measured symptom severity changes is not a feasible solution, because the same stimulus parameters have widely varying nerve activation properties not only between subjects, but within the same subject over time due to endogenous or exogenous factors that influence nerve fiber activation thresholds. This makes data interpretation in existing biomarker studies difficult.

TABLE 4

Candidate biomarkers of MDD

| Biomarker Type | Most Promising Marker | Specific Testable Null Hypothesis | Measurement Tools and Methods | Special Considerations[b] |
|---|---|---|---|---|
| immune | ↑ IL-6 and TNF-α in serum/plasma | $|IL-6|_{dep} = |IL-6|_{cont}$ | solid-phase ELISA on extracted plasma | fluctuating IL-6 level necessitates 24-hr assessment |
| endocrine | ↑ cortisol | $|cortisol|_{dep} = |cortisol|_{cont}$ | chemiluminescence-based assay on extracted plasma | fluctuating cortisol level necessitates 24-hr assessment |
| metabolic | ↓ blood flow | $Y_{bl,dep} = Y_{bl,cont}$ | SPECT | use $^{99m}$technetium-labelled HMPAO |
| metabolic | ↓ glucose metabolism | $|gluc|_{dep} = |gluc|_{cont}$ | PET (measure $^{18}$F-fluorodeoxyglucose metabolism in DLPFC) | use $^{18}$F-fluorodeoxyglucose |
| growth and survival | ↓ BDNF in serum | $|BDNF|_{dep} = |BDNF|_{cont}$ | ELISA on extracted serum | effective AD therapy should restore normal BDNF levels |
| structural | ↓ cholesterol | $|chol|_{dep+suicidal} = |chol|_{dep}$ | cholesterol assay on extracted serum | total cholesterol levels are significantly lower in suidical patients |
| structural/functional | ↓ folate in serum | $|folate|_{TRD} = |folate|_{dep}$ | folate assay on extracted serum | folate levels are significantly lower in refractory MDDs than in treatable MDDs |
| bioelectric | ↓ anterior cingulate activity | $I_{AC,dep} = I_{AC,cont}$ | scalp EEG (use 10/10 system referenced to left ear) | tomographic analysis necessary to localize current sources |
| functional | ↓ 5-HT1A receptor expression | $BP_{dep} = BP_{cont}$ | PET (measure 5-HT1A binding potential) | use [$^{11}$C]WAY-100635 selective 5-HT1A receptor ligand |
| functional | ↓ imipramine binding to 5-HTT on platelets | $B_{max,dep} = B_{max,cont}$ | PET (measure $B_{max}$ for $^3$H-imipramine binding in brain tissue) | use $^3$H-imipramine |

[a]Unless otherwise specified, information within Table 4 was adapted from Mossner et al., 2007
[b]At a minimum, control groups must be matched by age, gender, race, and socioeconomic status to accurately represent the general population of refractory MDD patients

[Abbr.: AD—antidepressant, BDNF—brain-derived neurotrophic factor, $B_{max}$—maximal affinity binding coefficient, BP—binding potential, ELISA—enzyme-linked immunosorbent assay, HMPAO—hexa-methyl propylene-amine-oxime, IL-6—interleukin-6, PET—positron-emission tomography, RN—raphe nucleus, SPECT—single photon emission computed tomography, TRD—treatment-resistant depression]. See R. Mossner, O. Mikova, E. Koutsilieri et al., "Consensus of the WFSBP Task Force on biological markers: Biological markers in depression," *The World Journal of Biological Psychiatry*, vol. 8, no. 3, pp. 141-174, 2007; S. Alesci, P. E. Martinez, S. Kelkar et al., "Major depression is associated with significant diurnal elevations in plasma interleukin-6 levels, a shift of its circadian rhythm, and loss of physiological complexity in its secretion: Clinical implications," *J Clin Endocrinol Metab*, vol. 90, pp. 2522-2530, 2005; S. D. Martin, E. Martin, S. S. Rai et al., "Brain blood flow changes in depressed patients treated with intemersonal psychotherapy or venlafaxine hydrochloride," *Arch Gen Psychiatry*, vol. 58, pp. 641-648, 2001; A. L. Brody, S. Saxena, P. Stoessel et al., "Regional brain metabolic changes in patients with major depression treated with either paroxetine or interpersonal therapy," *Arch Gen Psychiatry*, vol. 58, pp. 631-640, 2001; F. Karege, G. Perret, G. Bondolfi et al., "Decreased serum brain-derived neurotrophic factor levels in major depressed patients," *Psychiatry Research*, vol. 109, no. 2, pp. 143-148, 2002; E. Shimizu, K. Hashimoto, N. Okamura et al., "Alterations of serum levels of brain-derived neurotrophic factor (BDNF) in depressed patients with or without antidepressants," *Biol Psychiatry*, vol. 54, pp. 70-75, 2003; C. C. Allain, L. S. Poon, C. S. C. Chan et al., "Enzymatic determination of total serum cholesterol," *Clin Chem*, vol. 20, pp. 470-475, 1974; J. A. Golier, P. M. Marzuk, A. C. Leon et al., "Low serum cholesterol level and attempted suicide," *The American Journal of Psychiatry*, vol. 152, no. 3, pp. 419-423, 1995; H. Kunugi, N. Takei, H. Aoki et al., "Low serum cholesterol in suicide attempters," *Biol Psychiatry*, vol. 41, pp. 196-200, 1997; M. Fava, J. S. Borus, J. E. Alpert et al., "Folate, vitamin B12, and homocysteine in major depressive disorder," *Am J Psychiatry*, vol. 154, no. 3, pp. 426-428, 1997; D. Pizzagalli, R. D. Pascual-Marqui, J. B. Nitschke et al., "Anterior cingulate activity as a predictor of degree of treatment response in major depression: Evidence from brain electrical tomography analysis," *Am J Psychiatry*, vol. 158, no. 3, pp. 405-415, 2001; R. D. Pascual-Marqui, C. M. Michel, and D. Lehmann, "Low resolution electromagnetic tomography: A new method for localizing electrical activity in the brain," *Int J Psychophysiol*, vol. 18, pp. 49-65, 1994; Z. Bhagwagar, E. A. Rabiner, P. A. Sargent et al., "Persistent reduction in brain serotoninlA receptor binding in recovered depressed men measured by positron emission tomography with [11C]WAY-100635," *Molecular Psychiatry*, vol. 9, pp. 386-392, 2004; P. M. Ellis, and C. Salmond, "Is platelet imipramine binding reduced in depression? A meta-analysis," *Biol Psychiatry*, vol. 36, no. 5, pp. 292-299, 1994; and R. Raisman, D. Sechter, M. S. Briley et al., "High-affinity 3H-imipramine binding in platelets from untreated and treated depressed patients compared to healthy volunteers," Psychopharmacology, vol. 75, no. 4, pp. 368-371, 1981.

In an invasive treatment option for refractory MDD patients, an implantable neuromodulation device ideally: 1) remits depressive symptoms in a predictable, reproducible, and quantifiable manner without inducing the variable set of side effects observed with cunent therapies (i.e., stimulation of only the abnormally functioning neurocircuitry), 2) applies a focal connective stimulus (i.e., dose of therapy) only when the device confirms an impending relapse into a depressive episode, 3) autonomously learns and applies the most efficacious connective stimuli which correct for differing levels of biomarker abnormalities that correlate with patient specific depressive symptoms, 4) functions for the duration of a patient's lifetime without the need for secondary surgeries, and 5) stores and transmits peri-stimulus biomarker responses for off-line analyses. An open-loop system can meet criteria 4-5, however, a closed-loop system is needed to meet all five criteria.

Two requirements for an algorithm to autonomously optimize closed-loop treatment efficacy have been identified according to the present disclosure. First an autonomous closed-loop optimization algorithm requires a reproducible relationship between the applied stimulus parameters and the resulting disorder-specific biomarker responses (i.e., the applied therapeutic dose of charge and its rate of delivery using electrical stimulation, or the applied drug dose and its rate of delivery using chemical stimulation, should lead to predictable and reproducible restorative changes in the observed abnormal biomarker levels). Secondly, an autonomous closed-loop optimization algorithm requires a reproducible relationship between the magnitude and direction of biomarker abnormality connection (due the preceding applied stimuli) and the level of symptom remission. See C. E. Behrend, S. M. Cassim, M. J. Pallone et al., "Toward feedback controlled deep brain stimulation: Dynamics of glutamate release in the subthalamic nucleus in rats," *Journal of Neuroscience Methods*, vol. 180, pp. 278-289, 2009. While Behrend and colleagues recently demonstrated the feasibility of the former requirement, significant challenges remain with the latter due to a knowledge gap that remains between subjective reports of depressive symptoms and quantifiable levels of symptom-linked biomarker abnormality. However, groups seeking such knowledge for optimizing treatments in other neurological disorders have demonstrated promising progress toward this end. See C. E. Behrend, S. M. Cassim, M. J. Pallone et al., "Toward feedback controlled deep brain stimulation: Dynamics of glutamate release in the subthalamic nucleus in rats," *Journal of Neuroscience Methods*, vol. 180, pp. 278-289, 2009; A. C. Smith, S. A. Shah, A. E. Hudson et al., "A bayesian statistical analysis of behavioral facilitation associated with deep brain stimulation," *Journal of Neuroscience Methods*, vol. 183, pp. 267-276, 2009; and P. K. Wong, F. Yu, A. Shahangian et al., "Closed-loop control of cellular functions using combinatory drugs guided by a stochastic search algorithm," *PNAS*, vol. 105, no. 13, pp. 5105-5110, 2008.

Behrend et al. (2009) successfully demonstrated the feasibility of the first of the autonomous closed-loop optimization algorithm requirements by using closed-loop STN stimulation to maintain defined glutamate levels in the same structure. To do this, a transfer function was first derived to model the relationship between randomly patterned high-frequency stimulation pulse trains and extracellular glutamate dynamics in rat STN (The investigators applied pseudorandom binary sequences of stimulation pulses to the STN and used an autoregressive exogenous model to derive the transfer function). They found that 1) the derived transfer function accurately predicts the dynamic glutamate responses to unique pulse trains and that 2) on-demand STN stimulation sufficiently maintained the desired glutamate levels (i.e., Continuous or pre-programmed periodic stimulation is not necessary for effective control of biomarker levels; the desired biomarker levels in the STN can be maintained with on-demand stimulation using pulse train patterns with predictable effects on the biomarker level(s)). See C. E. Behrend, S. M. Cassim, M. J. Pallone et al., "Toward feedback controlled deep brain stimulation: Dynamics of glutamate release in the subthalamic nucleus in rats," *Journal of Neuroscience Methods*, vol. 180, pp. 278-289, 2009. If a predictable and reproducible relationship can be established between biomarker abnormality connection and depressive symptom relief, then Behrend et al.'s second finding also implies that withdrawal of the connective stimulus will not necessarily lead to a relapse.

To address the feasibility of the second autonomous closed-loop optimization algorithm requirement, reproducible and reliable relationships between the magnitude and direction of stimulus-associated biomarker abnormality correction and stimulus-associated depressive symptom relief must be established on a patient-to-patient basis. One proposed approach to surmounting this barrier is to subjectively assist (i.e., train) the treatment-optimization algorithm after the implantation recovery period. For example: after recovering from device implantation and before turning on the stimulation circuitry, a physician can program the device to measure the biomarker(s) of interest whenever the patient externally triggers it (e.g., an external piece of hardware, such as the wand-like device that a VNS implantee uses to externally trigger stimulation, can be used to wirelessly signal the implanted device to measure the biomarker of interest). See L. B. Marangell, M. Martinez, R. A. Jurdi et al., "Neurostimulation therapies in depression: A review of new modalities," *Acta Psychiatrica Scandinavica*, vol. 116, pp. 174-181, 2007. To subjectively assist the stimulus optimization algorithm and provide insight to the physician, the physician can instruct the patient to routinely assess their depressive symptom severity (e.g., using a standardized depression rating scale) while simultaneously signaling the device to measure the biomarker(s) of interest. Over time, a rough relationship between the biomarker levels and symptom severity in a particular patient can be established. Then, starting with stimulus parameter combinations that have shown therapeutic efficacy in other patients, the process can be repeated to derive a rough relationship between the magnitude/direction of stimulus-associated biomarker abnormality correction and the level of stimulus-associated depressive symptom relief. If such relationships are established, investigators can begin to bridge the knowledge gap that currently exists between subjective reports of depressive symptoms and quantifiable abnormalities in biomarker levels. With time, the device can autonomously fine-tune the most efficacious parameter sets that most efficiently lead to the desired outcomes (i.e., minimal dose, maximal antidepressant response, minimal side effects, maximal antidepressant durability, etc.).

A stochastic search algorithm design called a "Gur Game" can in theory optimize stimulation parameters based on a measured set of stimulus/biomarker response data from previous stimulations (see B-C in FIG. 1). See P. K. Wong, F. Yu, A. Shahangian et al., "Closed-loop control of cellular functions using combinatory drugs guided by a stochastic search algorithm," *PNAS*, vol. 105, no. 13, pp. 5105-5110, 2008; and B. Tung, and L. Kleinrock, "Using finite state automata to produce self-optimization and self-control," *IEEE Transactions on Parallel and Distributed Systems*, vol. 7, no. 4, pp. 439-448, 1996. As a stochastic search algorithm, the Gur Game treats parameters independently and autonomously varies parameters in order to maximize a global response variable (e.g., the downstream biomarker response to stimulation, which is mapped as a percent of the maximum antidepressant response). The stochastic nature of the search algorithm enables it to rapidly find parameter sets that maximize (i.e., optimize) the global response variable within a large multi-dimensional parameter search space (see B in FIG. 1). It is well suited for closed-loop applications, because 1) the underlying mechanisms of the antidepressant therapy are largely irrelevant to the algorithm, as it works solely to maximize a global response variable by manipulating parameter values within predefined safety limits (e.g., a symptom-linked biomarker can serve as the global response variable), 2) the performance does not significantly decrease with additional parameters, enabling non-biological properties such as power consumption to be included in the optimization scheme, and 3) the algorithm does not get trapped in local maxima. See P. K. Wong, F. Yu, A. Shahangian et al., "Closed-loop control of cellular functions using combinatory drugs guided by a stochastic search algorithm," *PNAS*, vol. 105, no. 13, pp. 5105-5110, 2008; B. Tung, and L. Kleinrock, "Using finite state automata to produce self-optimization and self-control," *IEEE Transactions on Parallel and Distributed Systems*, vol. 7, no. 4, pp. 439-448, 1996; and X. J. Feng, B. Greenwald, H. Rabitz et al., "Toward closed-loop optimization of deep brain stimulation for Parkinson's disease: Concepts and lessons from a computational model," *Journal of Neuroengineering*, vol. 4, no. 2, pp. L14-L21, 2007.

Accordingly, if the effects of VNS are due to activation of specific nerve fiber groups within the vagus nerve, then knowledge of the type, level and rate of nerve fiber activation is critical for advancing knowledge of VNS therapy and for discovering candidate symptom- or disorder-linked biomarkers suitable for use in closed-loop neuromodulation devices. Rather than reporting applied stimulus parameters and the associated effects on symptom severity in VNS studies, the nerve fiber activation levels in response to the applied stimulus parameters should be reported. If the nerve fiber activation level is held constant, then it can serve as a pseudoindependent variable so that researchers can investigate the mechanisms of action of VNS in a standardized manner (e.g., biomarker response data can be more easily interpreted and compared across studies). Maintaining a fixed nerve activation level can be especially useful for quantifying any symptom- or disorder-linked biomarker level changes in response to fixed levels of nerve fiber activation. The graded cortical responses observed by Woodbury and Woodbury (1990) in response to VNS at different stimulus intensities suggests that identifying relationships between nerve activation levels and biomarker responses is possible. See D. M. Woodbury, and J. W. Woodbury, "Effects of vagal stimulation on experimentally induced seizures in rats," *Epilepsia*, vol. 31, no. Suppl. 2, pp. S7-S19, 1990. Since Woodbury and Woodbury reported the observed cortical responses with respect to VNS intensity, and not nerve activation level, the relationship cannot be adequately quantified or compared to analogous relationships observed in different subjects (due to differing nerve activation properties). If the nerve fiber activation level is maintained with respect to the maximal level of nerve fiber activation in each subject (e.g., when all fibers are activated), then quantitative analyses and comparisons of data from VNS studies becomes feasible. Furthermore, if fixed nerve activation levels can be maintained, then the stimulus parameter adjustment/optimization period required of all VNS device recipients is hypothesized to become more efficient and effective.

An automated strength-duration curve-mapping algorithm is presented. It is designed to rapidly determine all stimulus pulse durations and amplitudes within the programmable range that yield a compound action potential (CAP) response of fixed magnitude relative to the maximal CAP response that occurs when all fibers of a given type are activated. The magnitude of a peak in a CAP response is directly proportional to the number of activated nerve fibers with similar activation and conduction properties; given the natural variation in fiber diameters and degrees of myelination, distinct fiber groups can be identified based on the measured conduction velocity of individual CAP response peaks. If the en or between the desired CAP magnitude and the observed CAP magnitude is used as negative feedback to adjust the amplitude or duration of the next applied pulse, then the nerve activation property-mapping algorithm can be used as a nerve activation clamp. In the latter implementation, the algorithm can be used to clamp the nerve activation level to any desired level between the minimal and maximal levels of activation for a particular group of fibers.

After fully testing and debugging the CAP/SD mapping algorithm in rat, its utility as an investigational and therapeutic tool may be demonstrated by employing it in a large-scale VNS study seeking to determine whether VNS imparts an antidepressive effect due to modulation of the cholinergic anti-inflammatory reflex. The tool can also be employed to re-evaluate the widely debated cortical de-synchronization hypothesis at fixed levels of nerve fiber activation in order to determine whether unmyelinated C fiber afferents play a role in the anticonvulsive effects of VNS.

The VNS literature was reviewed in order to find testable hypotheses of how VNS might alleviate depressive symptoms in patients that respond to the therapy (e.g., experience >50% reduction in depressive symptoms/severity with VNS based on one or more subjective depression rating scales). Since a robust biomarker of MDD does not yet exist, the effects of VNS in literature must be reported in a semi-quantitative or subjective manner. The presented algorithm is meant to push VNS research into a more standardized, quantitative domain so that its therapeutic mechanisms can be systematically delineated. Knowledge of the type, level and rate of nerve fiber activation associated with a therapeutic effect is essential; however, this information is seldom reported, as most investigators tend to treat the applied stimulus parameters as responsible for the therapeutic effect (Table 5).

The autonomous CAP/SD mapping algorithm measures evoked CAP response magnitudes, recorded at a fixed distance superior to the stimulating cathode, to estimate the level/type nerve fiber activation. Conduction velocity is used to identify distinct nerve fiber groups in the left cervical vagus nerve, referred to as A (fast, myelinated fibers), B (slow, myelinated fibers), or C (slow, unmyelinated fibers). Alternative naming conventions exist, however, the nomenclature of Woodbury and Woodbury (1990) are used in the preset disclosure. See D. M. Woodbury, and J. W. Woodbury, "Effects of vagal stimulation on experimentally induced seizures in rats," *Epilepsia*, vol. 31, no. Suppl. 2, pp. S7-S19, 1990. When recording at a fixed, known distance from the stimulating cathode, the individual nerve fiber action potentials in response to an applied stimulus will summate at the recording electrode to form individual peaks in the CAP response waveform separated in time due to the conduction velocities of the activated axons (i.e., conduction velocity is directly proportional to axon diameter and myelination). Since the individual nerve fiber activation threshold is inversely proportional to the square of its diameter, the CAP response is a graded response with a magnitude proportional to the number of fibers activated due to an applied stimulus of known intensity. The relationship between fiber diameter, conduction velocity and activation threshold for A, B and C fibers is summarized in Panel A. See Id.

TABLE 5

Overview of select animal studies on the therapeutic mechanisms of VNS for TLE

| Application/ Purpose | Species | Sample Size | Stimulus Parameters | Activation Data? | Main Findings |
|---|---|---|---|---|---|
| Epilepsy/ Determine effect of VNS on seizure activity | Rat | Not stated; Likely >1 in most experiments | Amp: 0-7.5 mA PW: 20-1000 µs PRF: 1-20 Hz On/Off: Not stated | Yes[1] | 1. C fiber activation at PRF >4 Hz is anticonvulsive, with an effect proportional to the number of C fibers activated 2. Optimal stimulus parameters for anticonvulsive effect →Amp; 0.2-0.5 mA/mm$^2$, PW: 0.5-1 ms; PRF: 10-20 Hz |
| Epilepsy/ Determine effect of VNS on neural activity | Rat | $N_{exp}$: 9 $N_{con}$: 9 | Amp: 1.0 mA PW: 500 µs PRF: 30 Hz On/Off: 30 s/5 min **3 hr duration | No | 1. Bilateral fos[3] expression Increase with VNS in the NTS, DMN, LC, cingulate, amygdala and hypothalamus, among others ($P < 0.001$) 2. No fos expression increase with VNS in the hippocampus or EC |
| Epilepsy/ Determine effects of mNTS GABA and glutamate levels on neural activity | Rat | A: 20 B: 4 C: 5 D: 5 | A. Muscimol: 256 pmol ($GABA_A$-receptor agonist) B. Bicuculline: 177 pmol ($GABA_A$-receptor antagonist) C. Kynurenate: 634 pmol (Glut-receptor antagonist) D. 5% Lidocaine: 100 nL (Local anesthetic) | N/A[2] | 1. Muscimol, kynurenate and lidocaine delivered to the mNTS reduced seizure activity, but bicuculline had no effect 2. mNTS inhibition is a key component of the anticonvulsive effect of VNS |

[1] Strength duration curves were measured in an anesthetized and unanesthetized rat to determine the stimulus parameters required for 50% maximal activation of A, B and C fibers, respectively. These curves appear to have been used to select stimulus amplitudes and pulse durations for all experiments in the study.
[2] The authors modeled the effects of VNS on glutamate and GABA levels in the mNTS in an effort to delineate the differential roles of glutamate and GABA transmission in the mNTS on seizure activity induced by PTZ or bicuculline
[3] fos is a protein expressed in proportion to cellular activity. See D. M. Woodbury, and J. W. Woodbury, "Effects of vagal stimulation on experimentally induced seizures in rats," *Epilepsia*, vol. 31, no. Suppl. 2, pp. S7-S19, 1990; D. K. Naritoku, W. J. Teny, and R. H. Helfert, "Regional induction of fos immunoreactivity in the brain by anticonvulsant stimulation of the vagus nerve," *Epilepsy Research*, vol. 22, pp. 53-62, 1995; and B. R. Walker, A. Easton, and K. Gale, "Regulation of limbic motor seizures by GABA and glutamate transmission in the nucleus tractus solitarius," *Epilepsia*, vol. 40, no. 8, pp. 1051-1057, 1999.

PANEL A $$d_{A-fiber} > d_{B-fiber} > d_{C-fiber}$$

$$[V_{A-fiber} \approx 90 - 30 \text{ m/s}] > $$

$$[V_{B-fiber} \approx 20 - 10 \text{ m/s}] > [V_{C-fiber} \approx 1.6 - 0.3 \text{ m/s}]$$

$$Thres_{act} \propto \frac{1}{d_{fiber}^2}$$

$$\therefore Thres_{act,A-fiber} < Thres_{act,B-fiber} << Thres_{act,C-fiber}$$

CAP response magnitude (i.e., peak-to-peak distance in differential recordings, or peak height in single-ended recordings) in relation to the maximal CAP response magnitude (i.e., the CAP response magnitude at which an increase in stimulus intensity does not produce an increase in CAP response magnitude) is used to estimate the level of A, B, and C fiber activation. Since the number of activated fibers is proportional to the magnitude of the recorded CAP response, the time at which the CAP travels past the recording electrodes (in relation to the time at which the stimulus was applied) provides information on the type of fiber activated. The maximal CAP response represents the summed action potentials from all A, B or C fibers in a stimulated nerve trunk.

A method of predicting all stimulus amplitudes and durations that yield a CAP response of fixed magnitude is needed. Strength-duration (SD) equations can be used for predictive purposes, but they are conventionally only used as a fitting function for a set of experimentally determined stimulus amplitudes and durations that yield 50% maximal activation of a given fiber type. For example, Woodbury and Woodbury measured vagal CAP responses in rat by progressively increasing stimulus amplitude at fixed durations until the maximal and 50% maximal CAP responses were observed. See Id. The resulting SD curve was used for stimulus parameter selection in multiple experiments on different subjects whose nerve activation properties may not have been the same as the source of the SD curve. This is clearly not the most efficient method of measuring SD curves (the tedious nature of the procedure may explain its lack of use), nor is it a practical approach for an automated CAP/SD mapping algorithm. However, a linear transformation of Georges Weiss' hyperbolic SD equation (Eq. 1) to a linear charge-duration equation holds the key to rapidly generating SD curves for any level of nerve fiber activation with relative ease.

$$HyperbolicForm: \frac{1}{t_{st}} \int_0^t I_{st} d\tau = \frac{I_{Rh}(t_{st} + \tau_{SD})}{t_{st}} = \bar{I}_{st} \quad (Eq. 1)$$

$$LinearForm: \bar{I}_{st} \cdot t_{st} = I_{Rh}(t_{st} + \tau_{SD}) = \bar{Q}_{st}$$

In Eq. 1, $I_{st}$ is the mean stimulus current amplitude (A), $t_{st}$ is the stimulus duration (s), IRh is the rheobase current (A), SSD is the membrane time constant (a ratio of the charge threshold for very short stimuli and IRh, with units of time) and $Q_{st}$ is the charge/phase of stimulation (i.e., the product of stimulus current/phase and duration/phase, with units of Coulombs). See H. Bostock, "The strength-duration relationship for excitation of myelinated nerve: Computed dependence on membrane parameters," *J. Physiol.*, vol. 341, pp. 59-74, 1983; and W. Irnich, "Georges Weiss' Fundamental Law of Electrostimulation is 100 years old," *PACE*, vol. 25, no. 2, pp. 245-248, 2001.

There are several properties of particular interest of the linear form of Weiss' SD equation: 1) The rheobase current is the slope of the line, 2) the membrane time constant, Isp, is the absolute value of the stimulus duration at which the line intersects the duration axis (i.e., zero charge axis), and 3) the product of the mean stimulus amplitude and the duration, QV, produces the same level of nerve fiber activation, implying that different pulse shapes having the same mean amplitude and duration will yield the same magnitude CAP response. See Id. Bostock, Burke and Mogyoros have shown that Georges Weiss' SD equation models experimentally determined SD curves much more accurately than Lapicque or Hill's SD equations. See H. Bostock, "The strength-duration relationship for excitation of myelinated nerve: Computed dependence on membrane parameters," *J. Physiol.*, vol. 341, pp. 59-74, 1983; H. Bostock, T. A. Sears, and R. M. Sherratt, "The spatial distribution of excitability and membrane current in normal and demyelinated mammalian nerve fibres," *J. Physiol.*, vol. 341, pp. 41-58, 1983; and I. Mogyoros, M. C. Kiernan, and D. Burke, "Strength-duration properties of human peripheral nerve," *Brain*, vol. 119, pp. 439-447, 1996. Mostly in the 1980s, Hugh Bostock generated computational models of myelinated nerve fiber excitation properties and employed Weiss' equation to demonstrate how changes in the nodal membrane change nerve excitability. See W. Irnich, "Georges Weiss' Fundamental Law of Electrostimulation is 100 years old," *PACE*, vol. 25, no. 2, pp. 245-248, 2001; and H. Bostock, T. A. Sears, and R. M. Sherratt, "The spatial distribution of excitability and membrane current in normal and demyelinated mammalian nerve fibres," *J. Physiol.*, vol. 341, pp. 41-58, 1983. He compared Weiss' SD equation to those of Lapicque and Hill, finding a consistently superior fit with Weiss' equation. Mogyoros and Burke later applied knowledge gained from Bostock's modeling efforts to a practical application. They employed the linear form of Weiss' SD equation for the purpose of tracking changes in the membrane time constants of peripheral motor and sensory fibers in order to detect changes in the nodal membrane due to peripheral nerve injury or disease. They showed that Weiss' equation consistently provided a superior fit to the experimentally measured SD data (over the Lapicque equation). In addition, they showed that 1) the predicted membrane time constants of similar fiber types remain approximately constant with increasing levels of nerve fiber activation, 2) that motor fibers and sensory fibers can be identified based on their predicted membrane time constants (e.g., unmyelinated sensory fibers have a much greater membrane time constant due to an increased membrane capacitance per unit area relative to myelinated motor fibers), and 3) that the membrane time constant could be accurately predicted from as few as 2 experimentally measured data points on the SD curve. Ironically, their method of SD curve generation was analogous to the method used by Woodbury and Woodbury, except 50 or more points were manually measured to find the membrane time constant, and subsequent data analyses proved that only 2 points were needed. See I. Mogyoros, M. C. Kiernan, and D. Burke, "Strengthduration properties of human peripheral nerve," *Brain*, vol. 119, pp. 439-447, 1996.

Figure 3:
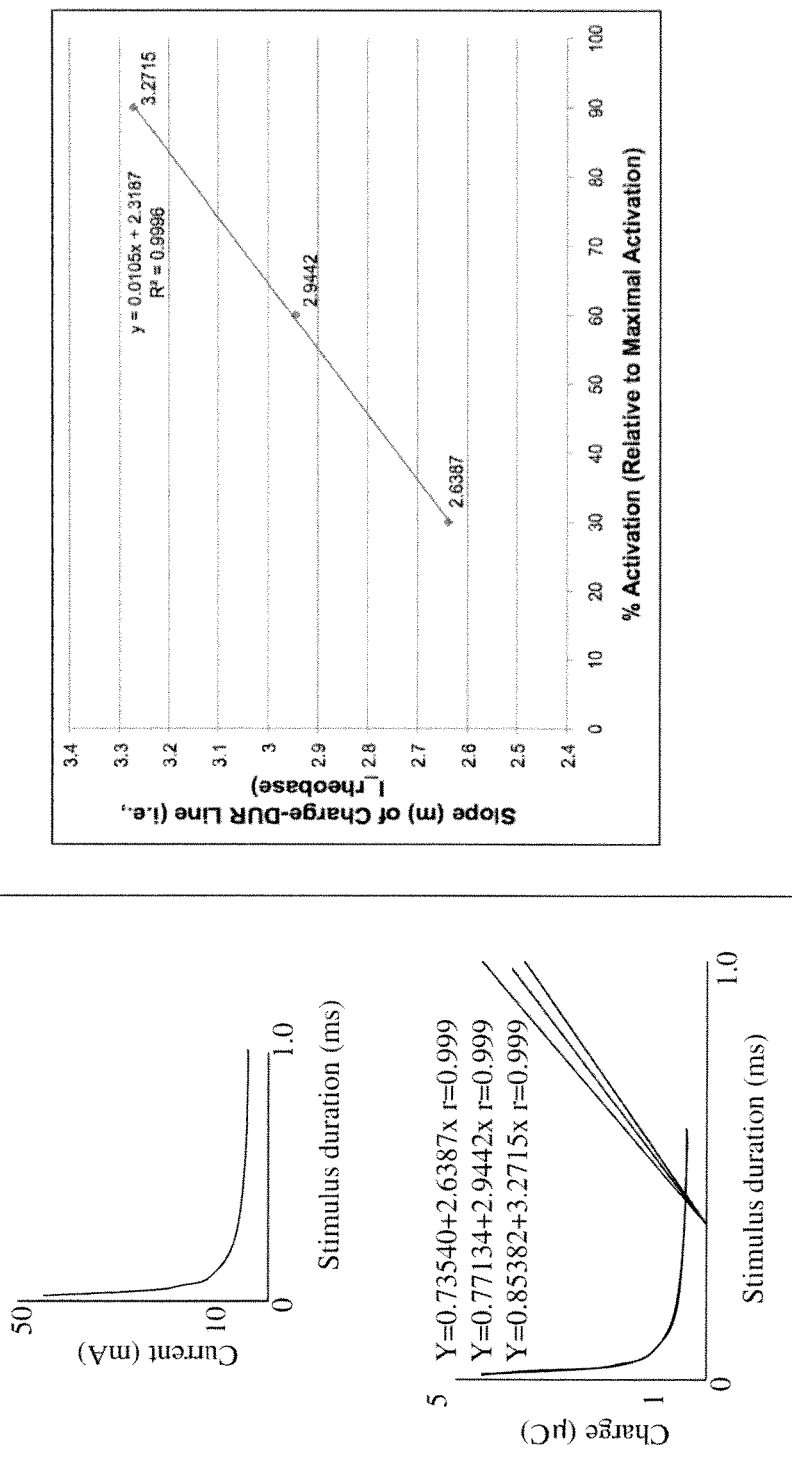

Data was extracted from FIG. 8 in Mogyoros et al., 1996 to test whether 1) the SD curve could be reconstructed from the charge-duration line and 2) whether there is a relationship between the rheobase current and the level of nerve fiber activation. The SD curve for 30, 60 and 90% maximal activation are easily reconstructed when enough charge-duration data points are available for an accurate estimation of $I_{Rh}$ (i.e., slope of line) and $r_{sD}$ (i.e., x-intercept of line), respectively. With their data, only 2/50 charge-duration data points were needed. When $I_{Rh}$ was plotted against percent maximal activation, a highly linear relationship was found. Referring to FIG. 3, the left hand side represents graphs showing 3 SD curves in hyperbolic and linear form where each curve represents the threshold for 30, 60 and 90% maximal activation, respectively (see Id.); and the right side represents plot of rheobase current versus % maximal activation (using data from Mogyoros et al.), demonstrating a highly linear relationship.

With the $I_{Rh}$ vs. percent maximal activation relationship and as few as two pulse amplitudes/durations that yield maximal and minimal activation of A, B or C fibers, it is possible to predict all pulse amplitudes and durations that yield any level of A, B or C fiber activation. For instance, if a few pulse amplitude/duration pairs that yield X % maximal B fiber activation are known, and (X−Fc) % activation is desired, how the stimulus amplitude or duration should be altered such that the (X−Fc) % activation level can be attained with one adjustment to either the stimulus amplitude or duration is determined by the authors of the present disclosure. To determine which adjustment to make, an estimate of $I_{Rh}$ for (X−Fc) % activation is obtained from the $I_{Rh}$ vs. percent maximal activation relationship. Since the membrane time constant, Tv), was found by Mogyoros and colleagues to be relatively constant at different levels of activation, the membrane time constant for X % activation is initially assumed to the be the same for (X−Fc) % activation. The $I_{Rh}$ and $r_{sD}$ estimates for (X−Fc) percentage activation are then substituted into Eq. 1 to obtain the new charge-duration line and strength-duration curve for (X−Fc) percentage maximal B fiber activation. Now, the pulse amplitude or width can be adjusted to evoke (X−Fc) % maximal activation. The process is summarized in Panel B, with X-Fc represented by X. A detailed flowchart is included in Appendix B, incorporated herein by reference in its entirety.

PANEL B $$WeissEq: Q_{st} = I_{st} \cdot t_{st} = I_{Rh}(t_{st} + \tau_{SD})$$

$$I_{st} = \frac{I_{Rh}(t_{st} + \tau_{SD})}{t_{st}} \Leftrightarrow \text{OR} \Leftrightarrow t_{st} = \frac{\tau_{SD} \cdot I_{Rh}}{I_{st} - I_{Rh}}$$

$$\text{If: } I_{st} = AMP_{\%Axt=\lambda} \wedge t_{st} = DUR_{\%Act=\lambda}$$

$$AMP_{\%Act=\lambda} = \frac{\hat{I}_{Rh,\%Act=\lambda}(DUR_{\%Act=\lambda} + \hat{\tau}_{SD,\%Act=\lambda})}{DUR_{\%Act=\lambda}}$$

$$y = f(x) = mx + b$$

$$\hat{I}_{Rh,\%Act=\lambda} = \hat{I}_{Rh,mod}(\% Act = \lambda) = \hat{m}_{mod} \cdot \lambda + \hat{b}_{mod}$$

$$\bar{\hat{\tau}}_{SD,\%Act=\lambda} = \text{mean}(\hat{\tau}_{SD,\%Act}) = \frac{1}{n}\sum_{i=1}^{n} \hat{\tau}_{SD,\%Act,i}$$

$$b = y - mx \Big|_{y=0, x=x\,int}$$

$$\hat{b}_{\%Act=\lambda} = \hat{Q}_{\%Act=\lambda} - \hat{I}_{Rh,\%Act=\lambda} \cdot DUR_{\%Act=\lambda} \Big|_{Q_{\%Act=\lambda}=0, DUR_{\%Act=\lambda}=\bar{\hat{\tau}}_{SD,\%Act=\lambda}}$$

$$\hat{b}_{\%Act=\lambda} = \hat{I}_{Rh,\%Act=\lambda} \cdot \bar{\hat{\tau}}_{SD,\%Act=\lambda}$$

$$NewLineEqn: \hat{Q}_{\%Act=\lambda} =$$
$$\hat{I}_{Rh,\%Act=\lambda} \cdot DUR_{\%Act=\lambda} + \hat{b}_{\%Act=\lambda}$$

To compensate for any predictive errors or changes at the electrode-tissue interface, an error signal, derived from the difference between the observed and desired CAP response, can be used to proportionately adjust the stimulus amplitude or duration of the next applied pulse such that the nerve fiber group is clamped at any desired level of maximal activation. This idea was inspired by a Bostock and Burke review of nerve excitation threshold tracking for the purpose of investigating "metabolic and toxic neuropathies". See H. Bostock, K. Cikurel, and D. Burke, "Threshold tracking techniques in the study of human peripheral nerve," *MUSCLE & NERVE*, vol. 21, pp. 137-158, 1998. Specifically, their "Threshold Tracker" looks for changes in nerve excitability at the site of stimulation due to any endogenous or exogenous factor that may affect nerve excitability (e.g., temperature, toxins, diabetic neuropathy, ischemia, etc.). Their algorithm generates SD curves much like Woodbury and Woodbury did, but then uses an error signal to adjust stimulus amplitude such that a fixed level of nerve activation is maintained. They too failed to recognize the advantages of using Weiss' charge-duration line equation and the relationship between 1Rh and percent maximal activation as a tool for predicting stimulus parameters that yield any level of activation. This predictive tool can become especially important in therapeutic nerve stimulation applications (e.g., VNS), because the therapeutic parameter settings can be based on discrete levels of vagal A, B, or C fiber activation. Any of the pulse amplitudes or durations that are predicted to yield the desired CAP response (i.e., percentage activation) can be applied, leaving the pulse repetition frequency (PRF) as the key tuning parameter for optimizing the therapy. Furthermore, nerve activation levels associated with an optimal therapeutic effect (based on subjective accounts or quantifiable biomarkers) can be used to develop standardized dosing schemes over time. Since the same parameters have widely varying effects from patient to patient, these types of analyses are not currently possible.

Figure 4:
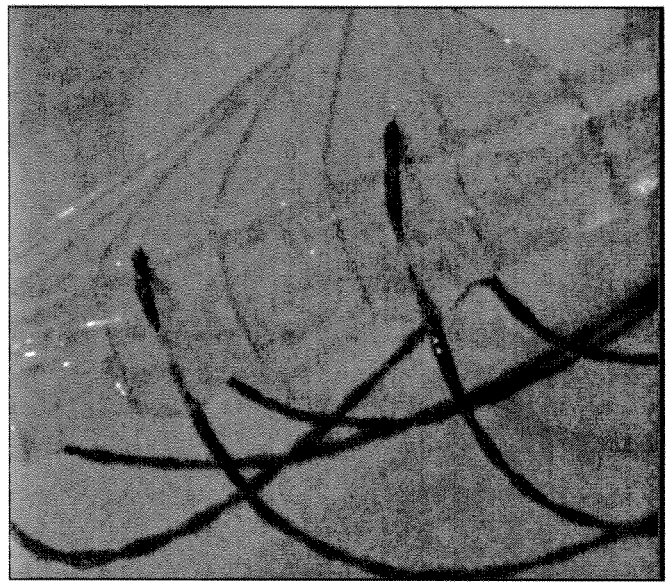
FIG. 4 represents schematic pictures of the experimental setup and electrode used according to the present disclosure.
Figure 4:
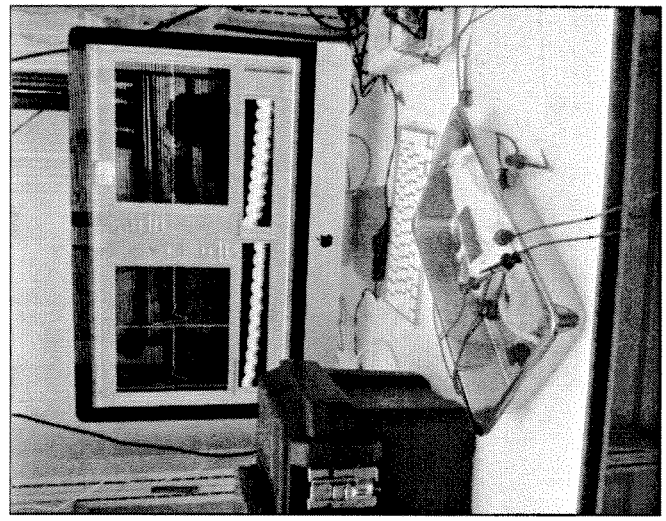
Figure 4:
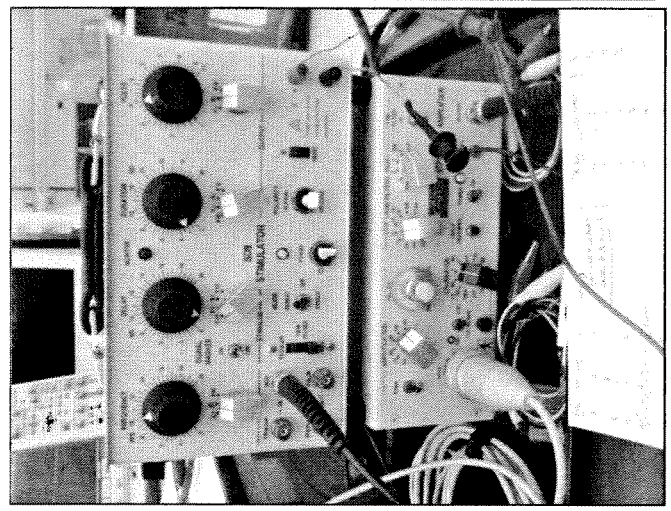

As a proof of concept, the predictive power of the CAP/SD mapping algorithm was tested on a rat sciatic nerve in situ. Immediately following the decapitation of a Sprague-Dawley rat (provided by Seth Wilks from Dr. Kevin Otto's lab), the right sciatic nerve was exposed (decapitation precluded vagal nerve stimulation) and bathed in warm artificial cerebrospinal fluid (fresh, warm media was applied every 10 minutes). A custom-made silicon cuff electrode (MicroProbes, Inc.) with 8 2-mil diameter Pt/Ir sites (0.5 mm inner cuff diameter; 1 0 mm site spacing) was wrapped around the sciatic nerve. The output terminals of a constant voltage, biphasic Grass stimulator were then connected to channels 1 and 2 of the cuff electrode (anode to channel 1 and cathode to channel 2). A Grass differential amplifier was connected to channels 6-8 of the cuff electrode (common/ground to channel 6, non-inverting input to channel 7 and inverting input to channel 8). The output of the Grass amplifier was digitized by a NI-USB 6259 multifunction DAQ, where it was sampled at 25 kHz and plotted/saved using custom-made Labview recording software. The Labview software was used to trigger the Grass stimulator to stimulate at the programmed settings for 5 s and to trigger the recording as soon as the stimulation started. Two points on a strength duration curve were manually determined using the CAP response magnitude of the fastest identifiable fiber group in Trial 11 as the first of the points (CAPPk2Pk, T11-=1.3 V after 1000× gain I $DUR_{st}$: 1 ms; $AMP_{st}$: 4 V; $PRF_{st}$: 10 Hz). The CAP magnitude was visually estimated from 1/50 CAP responses that were recorded for each trial (5 s train duration×10 Hz PRF=50 applied biphasic pulses and associated CAP responses). It took 11 more trials to manually determine the second point on the SD curve (CAPpk2pk, T22 1.3 V after 1000× gain I $DUR_{st}$: 0.5 ms; $AMP_{st}$: 6 V; $PRF_{st}$: 10 Hz). At this point in the experiment, an undergraduate assistant was asked to convert the two points on the SD curve to charge-duration format (A constant current stimulator was not available at the time of the experiment, so a constant voltage stimulator was used; therefore, the data is not truly in charge-duration format, but related through Ohm's law). The assistant was then instructed to quickly estimate the slope of a line passing through the 2 manually determined charge-duration data points and to then suggest other pulse durations and amplitudes that fall on that line. Using this method, 4 additional points on the SD curve were predicted and verified in Trials 26-33. To be certain that the results were not artificial, random parameters were applied and replicate trials were performed in Trials 28-29 and Trials 31-32. FIG. 4 shows the experimental setup and electrode used for this experiment.

Figure 5:
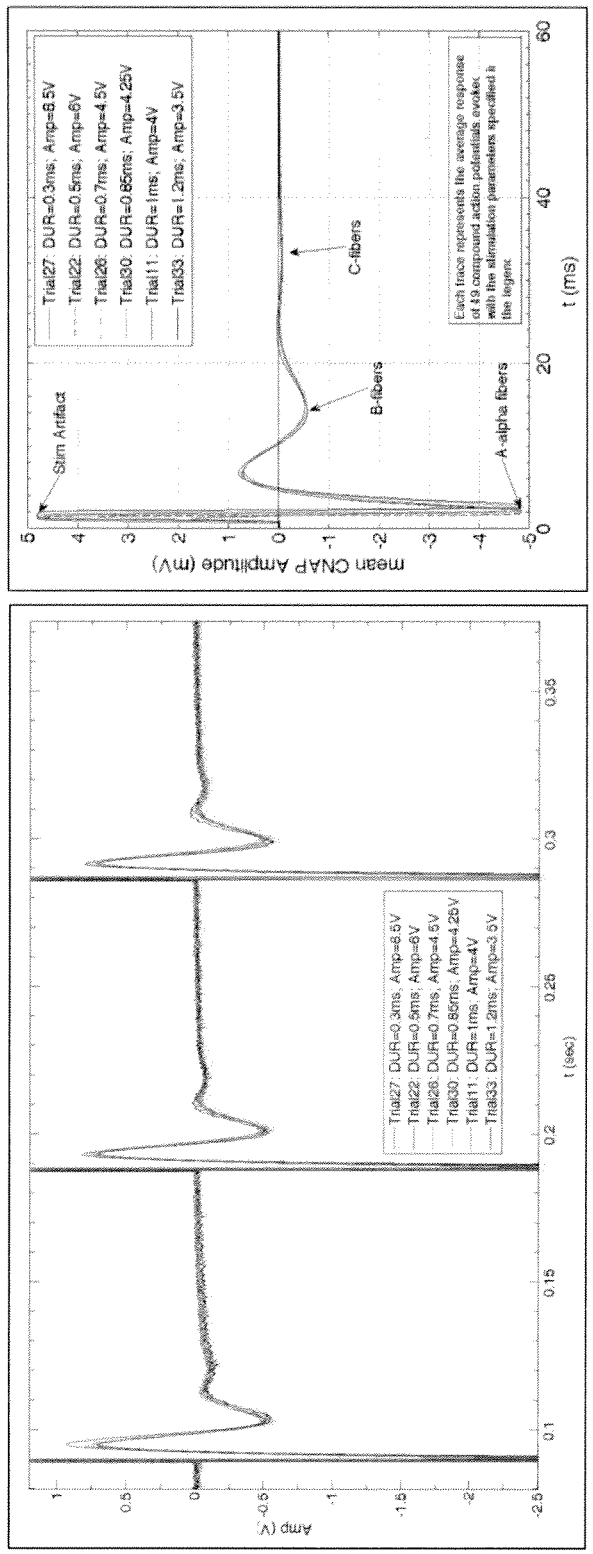
FIG. 5 represents an overlay of the raw compound action potential (CAP) responses and an overlay of the mean CAP responses evoked with the 6 duration/amplitude pairs.

Using Matlab R2010a, a post-experimental analysis was performed on the CAP responses evoked with the 6 applied pulse duration and amplitude pairs on the SD curve (2 manually determined points and 4 predicted points). FIG. 5 shows an overlay of the raw CAP responses and an overlay of the mean CAP responses evoked with the 6 duration/amplitude pairs. The recording software was triggered only after the first stimulus pulse was applied; therefore, only 49/50 responses recorded in each trial are represented in the mean CAP response overlay plot. Note how accurate the predictions were, even in the raw CAP response overlay plot. Three distinct peaks are evident in FIG. 5 [Right]. The first peak is partially masked by the stimulation artifact due to the short separation distance between the stimulating and recording electrodes (5 mm spacing between the stimulating cathode and the non-inverting terminal of the recording amplifier). However, the consistency of the response supports the utility of the prediction method. Furthermore, the ease of the method makes an autonomous algorithm feasible.

An additional analysis was performed on the 6 SD curve data points to verify the proposed method of determining the best-fit charge-duration line and reconstructing the SD curve. Panel C provides an overview of the regression method applied to determine the best-fit charge duration line. The goodness-of-fit (i.e., $R^2$) metric and membrane time constant were also estimated. For a more detailed overview of the algorithm, please refer to the flowcharts provided in Appendix B.

Figure 6:
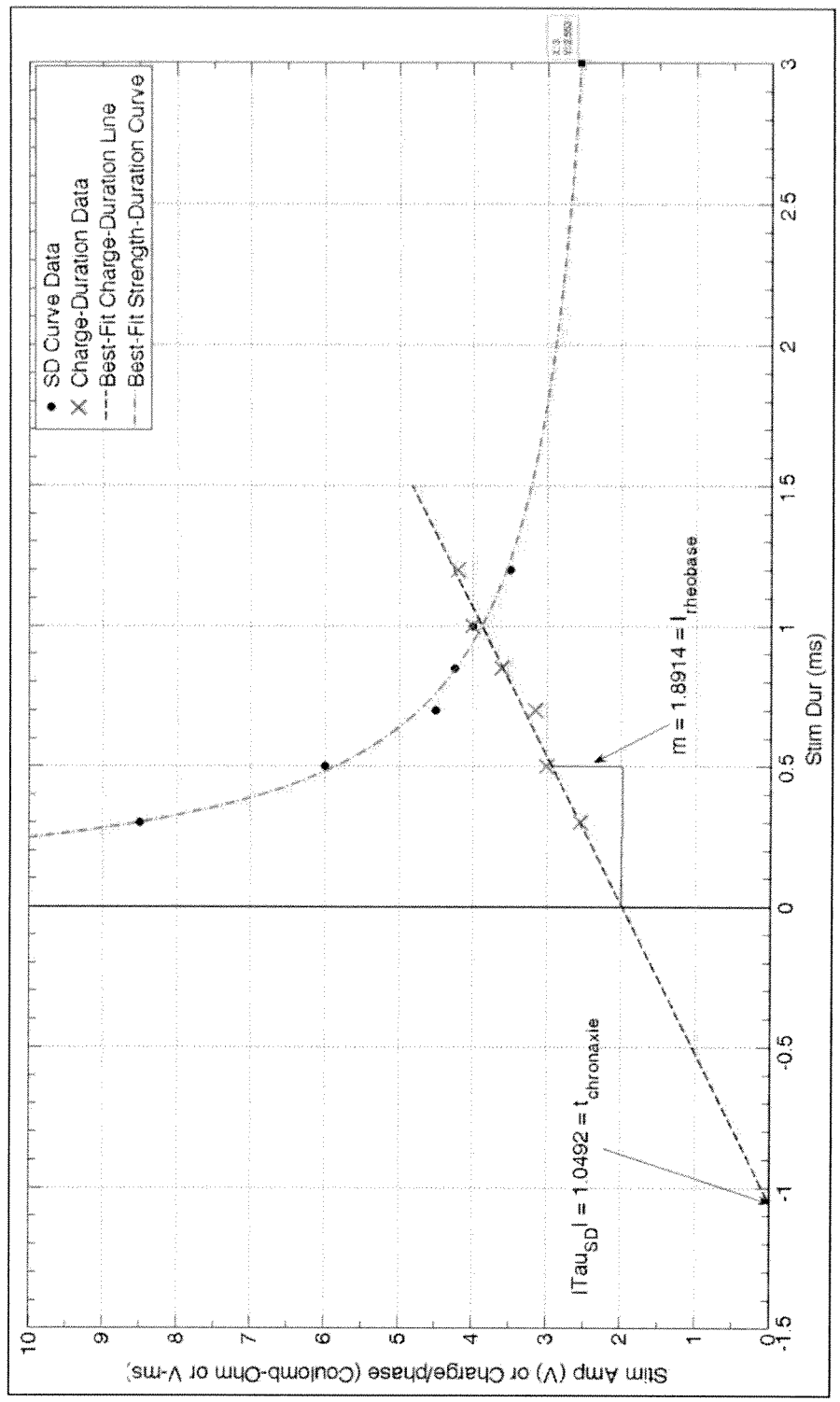
FIG. 6 represents the results of applying the method outlined in Panel C and Appendix B.
Figures 7A, 7B, 7C:
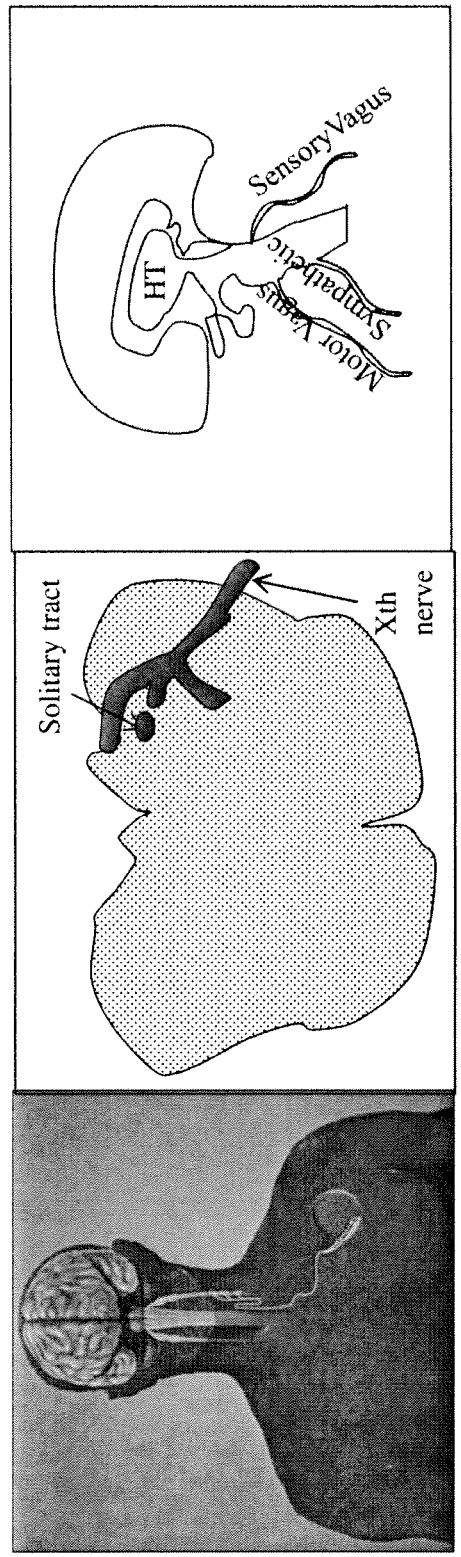
FIG. 7 represents a VNS device housing and electrode implant location (FIG. 7A); a cross-section of a human brainstem showing the primary sites of vagal input (FIG. 7B), and a summary of NTS efferent projections that impart diffuse, nerve activation level and rate-dependent effects on CNS function is depicted (FIG. 7C), according to the prior art.
Figure 8A:
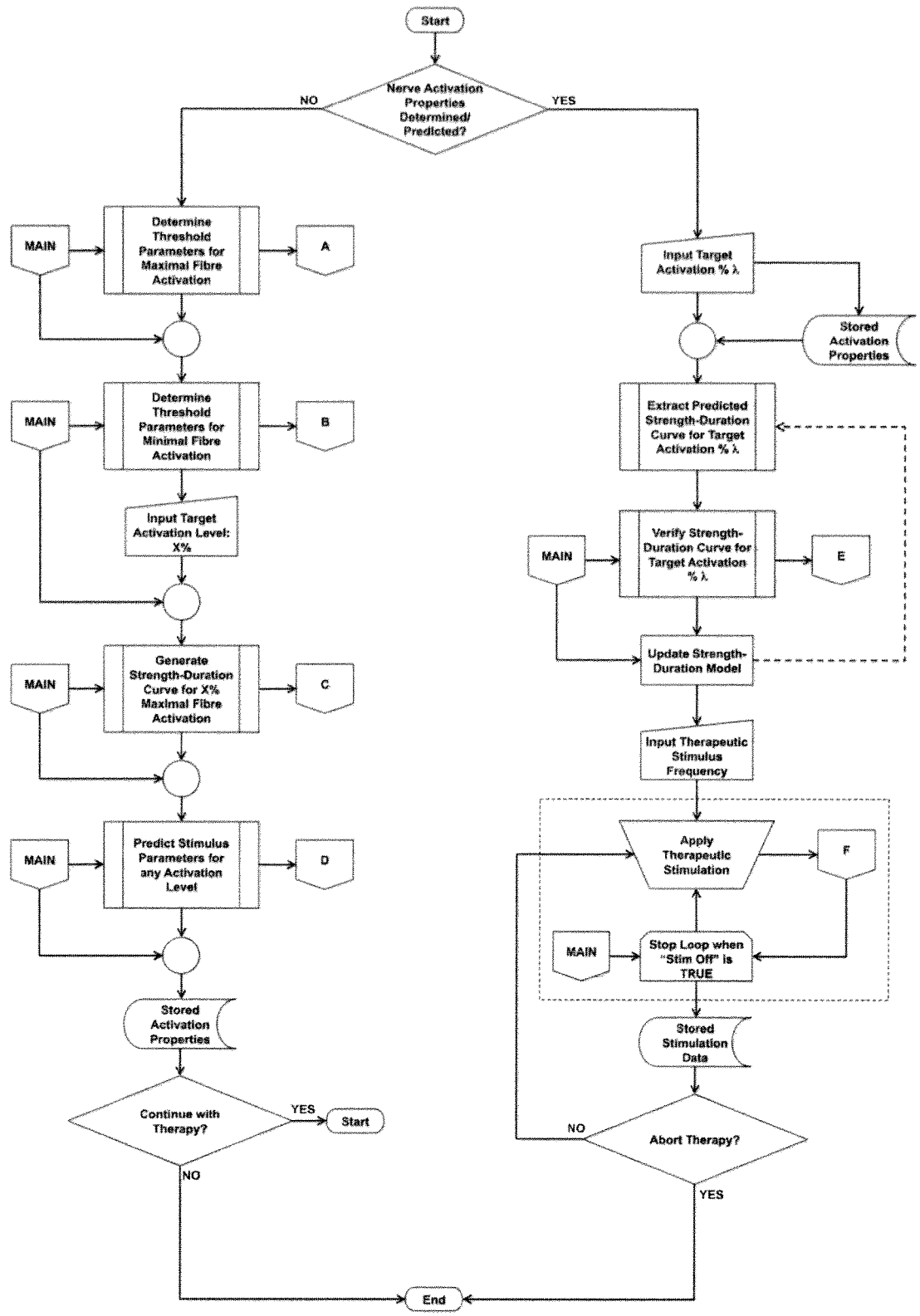
FIGS. 8A-8F illustrate a flow chart in accordance with the present invention.
Figure 8B:
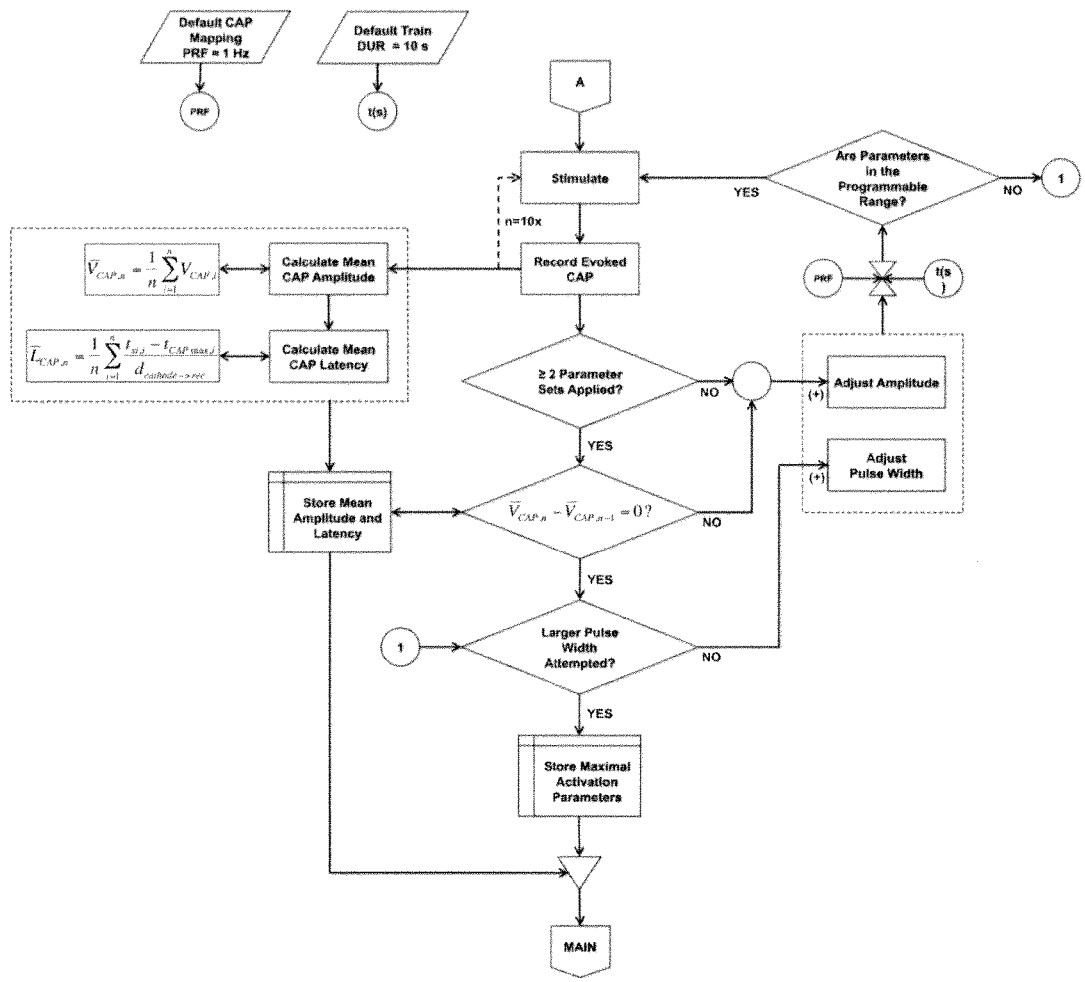
Figure 8C:
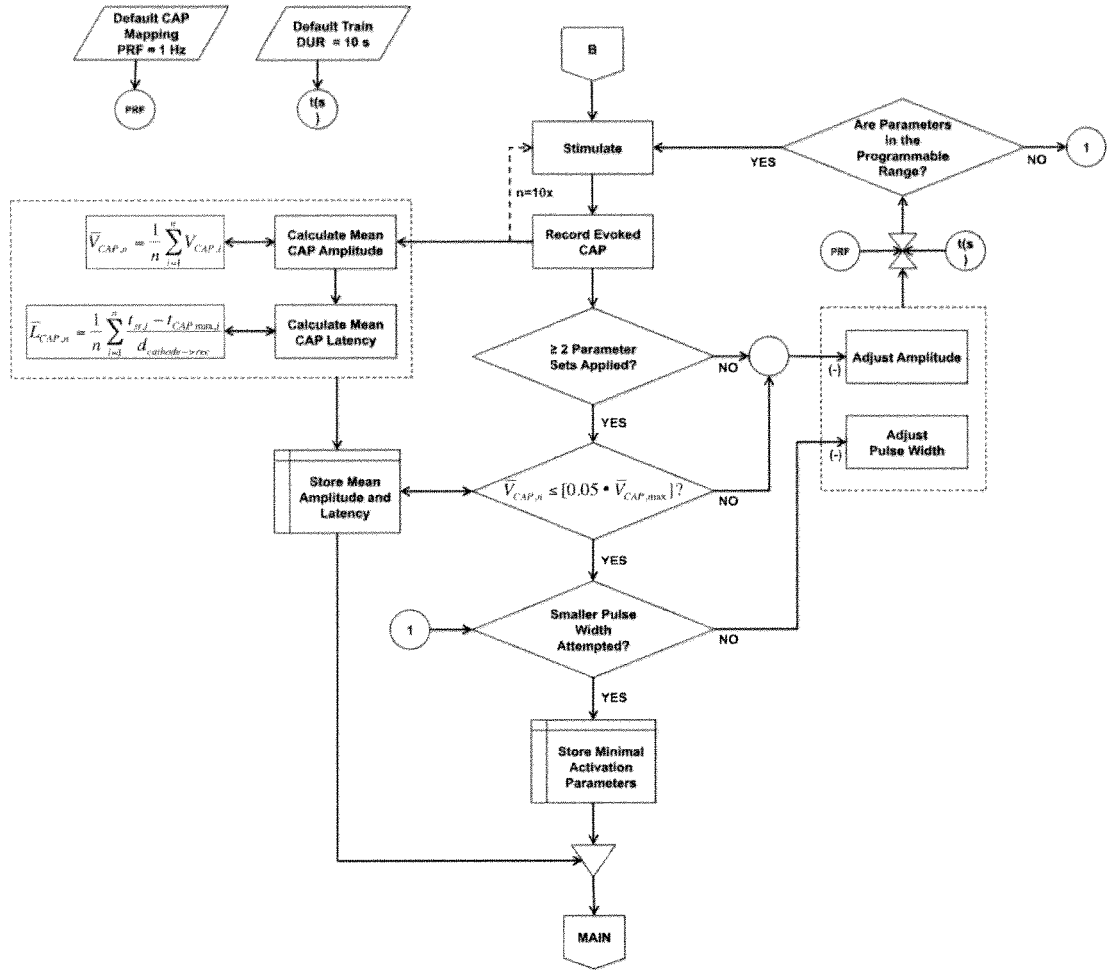
Figure 8D:
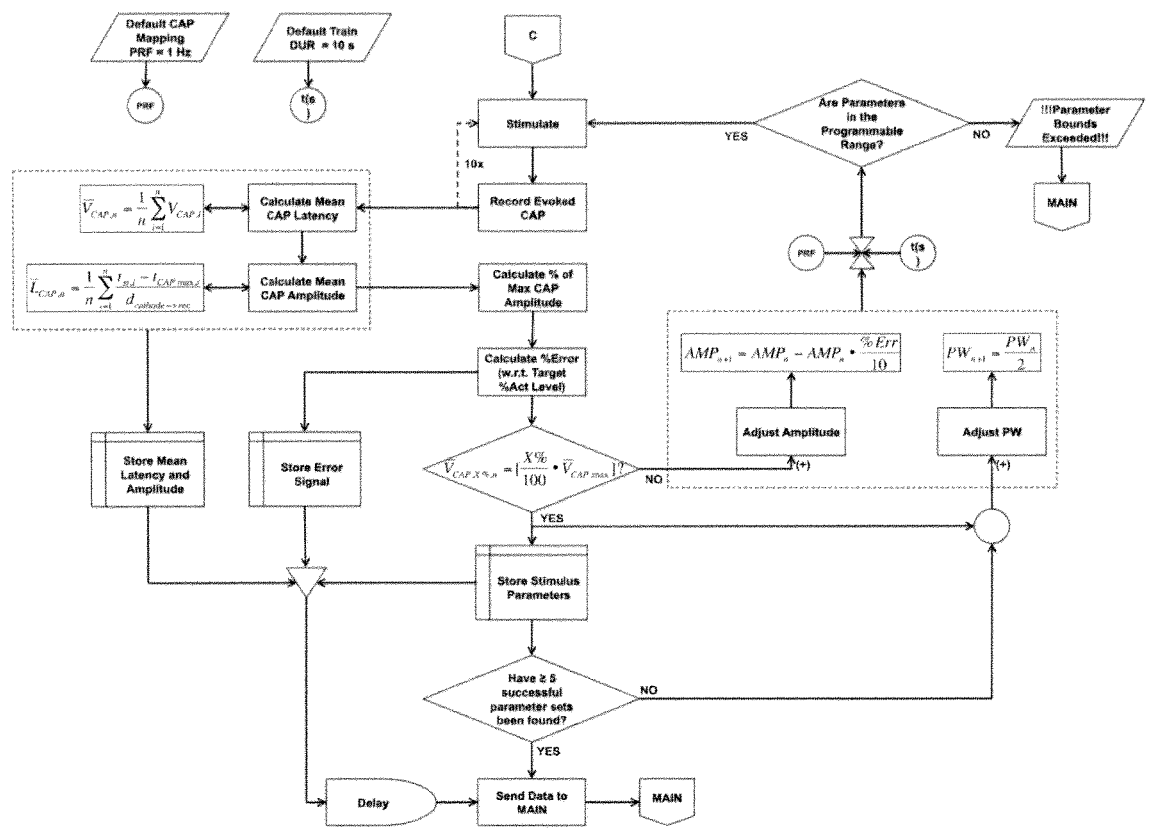
Figure 8E:
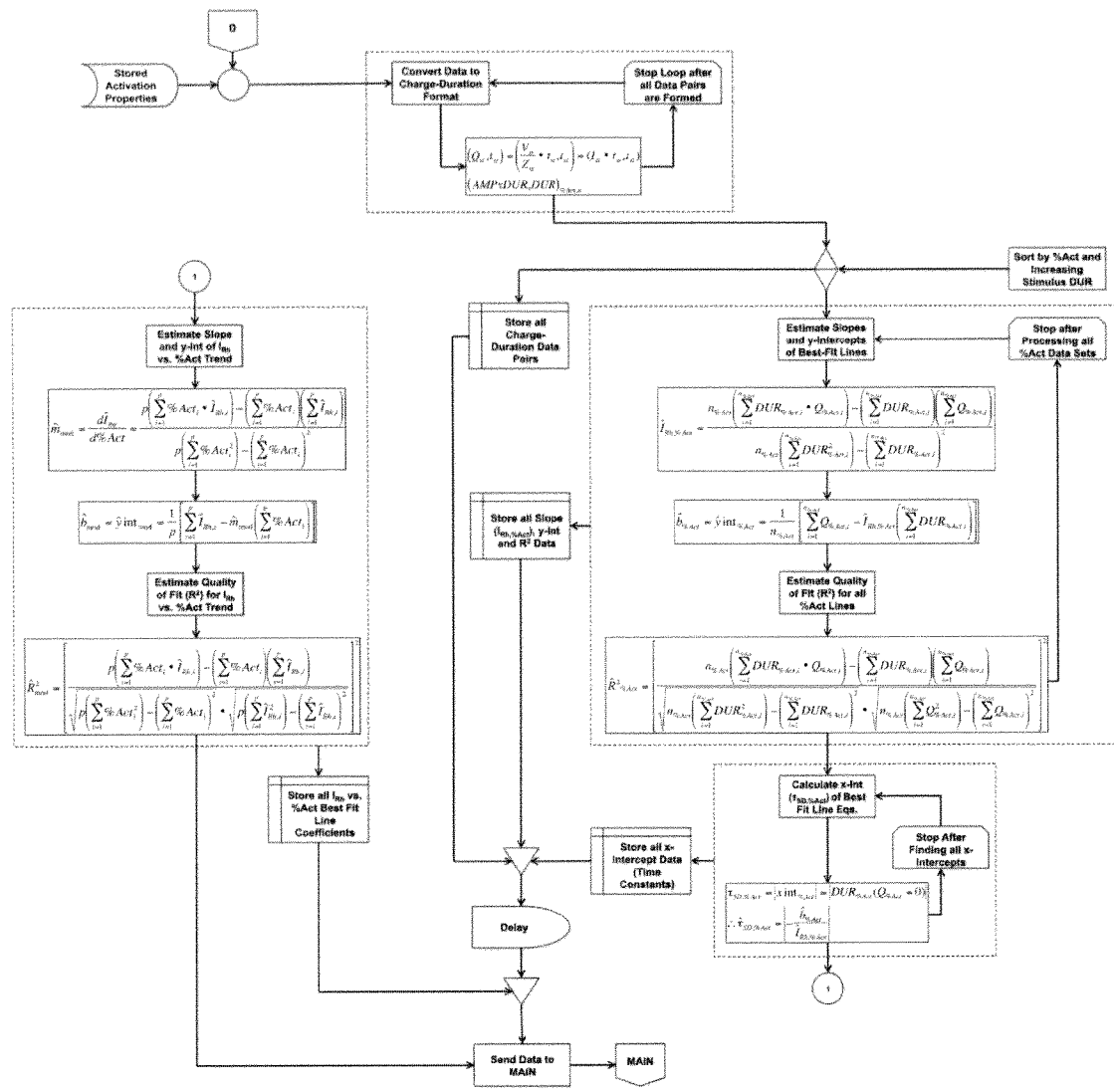
Figure 8F:
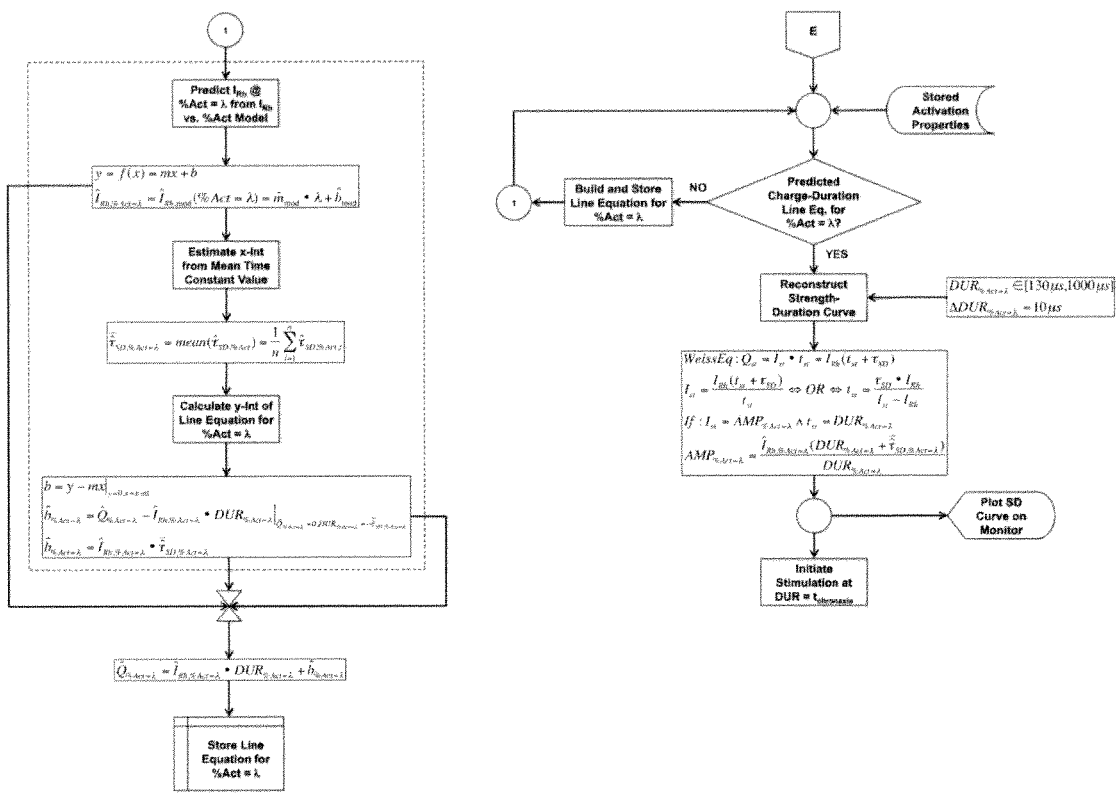

FIG. 6 shows the results of applying the method outlined in Panel C and Appendix B. It is worth noting that the true rheobase current is 1.8914 V divided by the load impedance (~20 km, translating to approximately 94.57p,A. However, the data demonstrate that the prediction method works with biphasic, constant-voltage rectangular waveforms. Linear regression yielded a best-fit line to the 6 charge-duration data pairs with an $R^2$ of 0.9755 and an estimated membrane time constant of 1.0492 ms. Using the slope (i.e., $I_{Rh}$) and x-intercept (i.e., $r_{sD}$) of the best-fit line, the hyperbolic form of the Weiss equation (Eq. 1) was reconstructed (over a 3 ms window) and plotted over the 6 data points on the SD curve. Accordingly, the reconstructed SD curve fit the data.

With 2 manually measured points on an SD curve, all pulse amplitudes and durations that yield the desired CAP response magnitude (and by inference, the desired proportion of A, B or C fiber activation) can be predicted using a transformation of the Georges Weiss' hyperbolic strength-duration equation. See W. Imich, "Georges Weiss' Fundamental Law of Electrostimulation is 100 years old," *PACE*, vol. 25, no. 2, pp. 245-248, 2001. Since all amplitudes and durations that yield the desired level/type of nerve fiber activation are known when using the algorithm, pulse repetition frequency (PRF) remains as a key tuning parameter for maximizing the therapeutic response to VNS at a fixed level of nerve activation. The relationship between the rheobase threshold current and the percent of maximal activation was found to be approximately linear, implying that the method of using CAP magnitude to estimate the number of activated fibers is valid. The aforementioned relationships can be used to predict sets of pulse amplitudes and durations that yield any desired level of nerve fiber activation with excellent accuracy, significantly simplifying the stimulus parameter selection process and the number of test measurements that are needed to map the activation properties of patients.

PANEL C $$(Q_{st}, t_{st}) = \left(\frac{V_{st}}{Z_{st}} \cdot t_{st}, t_{st}\right) = (I_{st} \cdot t_{st}, t_{st})$$

$$(AMPxDUR, DUR)_{\%Act,n}$$

$$\hat{I}_{Rh,\%Act} = \frac{n_{\%Act}\left(\sum_{i=1}^{n_{\%Act}} DUR_{\%Act=\lambda,i} \cdot Q_{\%Act,i}\right) - \left(\sum_{i=1}^{n_{\%Act}} DUR_{\%Act=\lambda,i}\right)\left(\sum_{i=1}^{n_{\%Act}} DUR_{\%Act,i}\right)}{n_{\%Act}\left(\sum_{i=1}^{n_{\%Act}} DUR_{\%Act,i}^2\right) - \left(\sum_{i=1}^{n_{\%Act}} DUR_{\%Act,i}\right)^2}$$

$$\hat{b}_{\%Act} = \hat{y}int_{\%Act} = \frac{1}{n_{\%Act}}\left[\sum_{i=1}^{n_{\%Act}} Q_{\%Act,i} - \hat{I}_{Rh,\%Act}\left(\sum_{i=1}^{n_{\%Act}} DUR_{\%Act,i}\right)\right]$$

$$\hat{R}^2_{\%Act} =$$

$$\left[\frac{n_{\%Act}\left(\sum_{i=1}^{n_{\%Act}} Q_{\%Act,i} \cdot Q_{\%Act,i}\right) - \left(\sum_{i=1}^{n_{\%Act}} DUR_{\%Act,i}\right)\left(\sum_{i=1}^{n_{\%Act}} Q_{\%Act,i}\right)}{\sqrt{n_{\%Act}\left(\sum_{i=1}^{n_{\%Act}} DUR_{\%Act,i}^2\right) - \left(\sum_{i=1}^{n_{\%Act}} DUR_{\%Act,i}\right)^2} \cdot \sqrt{n_{\%Act}\left(\sum_{i=1}^{n_{\%Act}} Q_{\%Act,i}^2\right) - \left(\sum_{i=1}^{n_{\%Act}} Q_{\%Act,i}\right)^2}}\right]^2$$

$$\tau_{SD,\%Act} = |x\, int_{\%Act}| = |DUR_{\%Act}(Q_{\%Act} = 0)|$$

$$\therefore \hat{\tau}_{SD,\%Act} = \left|-\frac{\hat{b}_{\%Act}}{\hat{I}_{Rh,\%Act}}\right|$$

A wealth of evidence, starting with the work of Bulloch, Hall and Goldstein in the 1980s, has shown that the immune system communicates with the CNS through humoral and neural pathways. These "immunoregulatory circuits" link the CNS and the immune system, with bidirectional influences on their respective functions. See G. M. Shepherd, *Neurobiology*, 3rd ed., New York: Oxford University Press, Inc., 1994. The most studied and perhaps most important immunoregulatory circuit is the hypothalamic-pituitary-adrenal (I-IPA) axis (However, the cholinergic anti-inflammatory reflex may soon be a contender, since it is the fastest means of CNS-mediated control over immune function). See K. J. Tracey, "Reflex control of immunity," *Nature Review Immunology*, vol. 9, pp. 418-428, 2009; C. L. Raison, L. Capuron, and A. H. Miller, "Cytokines sing the blues: Inflammation and the pathogenesis of depression," *TRENDS in Immunology*, vol. 27, no. 1, pp. 24-31, 2006; and C. B. Nemeroff, E. Widerlov, G. Bissette et al., "Elevated concentrations of CSF corticotropin-releasing factor-like immunoreactivity in depressed patients," *Science*, vol. 226, no. 4680, pp. 1342-1344, 1984. Corticotropin releasing hormone (CRH), a hormone produced and released from the paraventricular nucleus (PVN) of the hypothalamus in response to physical and mental stress, injury and/or infection, promotes lymphocyte proliferation (e.g., natural killer cells, B cells and T cells). CRH and vasopressin released from the PVN of the hypothalamus then act on the anterior pituitary gland to promote adrenocorticotropin releasing hormone (ACM) production and release into circulation. As the name implies, ACTH travels through the circulatory system to the adrenal cortices, where it promotes glucocorticoid (i.e., stress hormone, or cortisol) production and release. Circulating glucocorticoids (GC) then impart negative feedback to the hypothalamus and pituitary gland to inhibit CRH and ACM production. At high concentrations, GCs suppress lymphocyte proliferation. Thus, CRH and GCs have opposing regulatory effects on immune function. See J. E. Blalock, "The immune system as a sensory organ," *J Immunol*, vol. 132, pp. 1067-1070, 1984; and J. E. Blalock, and E. M. Smith, "The immune system: our mobile brain?," *Immunology Today*, vol. 6, no. 4, pp. 115-117, 1985. This led Blalock and Smith (1985) to suggest that the immune system is actually a "mobile brain," or a type of sixth sense, that bi-directionally interacts with the CNS. See J. E. Blalock, "The immune system as a sensory organ," *J Immunol*, vol. 132, pp. 1067-1070, 1984; and J. E. Blalock, and E. M. Smith, "The immune system: our mobile brain?," *Immunology Today*, vol. 6, no. 4, pp. 115-117, 1985. They suggest that stress, implied by the level of unbound GCs in circulation, originating from physical, psychological and/or immune stressors, have bidirectional influences on neural and immune function. For unknown reasons, most MDD patients show GC resistance, characterized by a reduced strength of GC-mediated negative feedback on CRH and ACM production. See G. M. Shepherd, *Neurobiology*, 3rd ed., New York: Oxford University Press, Inc., 1994; and H. O. Besedovsky, A. E. del Rey, and E. Sorkin, "Immune-Neuroendocrine Interactions," *The Journal of Immunology*, vol. 135, no. 2, pp. 750s-754s, 1985.

PICs, including tumor necrosis factor-alpha (TNF-a), interleukin-6 (IL-6) and interleukin-1beta (IL-1b) among others, have profound influences on inflammatory processes, behaviors, emotions and general CNS function. See G. Cizza, A. H. Marques, F. Eskandari et al., "Elevated neuroimmune biomarkers in sweat patches and plasma of premenopausal women with major depressive disorder in remission: The POWER study," *Biol Psychiatry*, vol. 64, pp. 907-911, 2008; S. Alesci, P. E. Martinez, S. Kelkar et al., "Major depression is associated with significant diurnal elevations in plasma interleukin-6 levels, a shift of its circadian rhythm, and loss of physiological complexity in its secretion: Clinical implications," *J Clin Endocrinol Metab*, vol. 90, pp. 2522-2530, 2005; and R. Dantzer, and K. W. Kelley, "Twenty years of research on cytokine-induced sickness behavior," *Brain, Behavior, and Immunity*, vol. 21, pp. 153-160, 2007. Inflammation or infection in the periphery is communicated to the CNS through the action of PICs and antigens of pathogenic bacteria that are recognized by the innate immune system. These signals are conveyed to the CNS through a redundant set of humoral and neural pathways, where they are amplified by resident microglia. See R. Dantzer, J. C. O'Connor, G. G. Freund et al., "From inflammation to sickness and depression: When the immune system subjugates the brain," *Nature Reviews Neuroscience*, vol. 9, pp. 46-56, 2008. In the humoral pathway, certain inflammatory mediator molecules, such as IL-1a, IL-1b and TNF-α, as well as pathogenic antigens referred to as "pathogen associated molecular proteins" (PAMPs), signal the presence of peripheral inflammation or infection to the CNS via an incomplete blood-brain bather (BBB) lining the ventricular system at the level of the circumventricular organs. See Id.; and J. Licinio, and M.-L. Wong, "The role of inflammatory mediators in the biology of major depression: central nervous system cytokines modulate the biological substrate of depressive symptoms, regulate stress-responsive systems, and contribute to neurotoxicity and neuroprotection," *Molecular Psychiatry*, vol. 4, pp. 317-327, 1999. Although not known with certainty, it is believed that PICs diffuse into the circumventricular organs, where they activate microglia lining the choroid plexus and meninges. In one route, microglia are activated through binding to an IL-1 receptor. In an alternative route, microglia are activated by PAMPs binding to specialized toll-like receptors. Activated microglia from both humoral routes then upregulate the transcription of certain enzymes and PICs, namely IL-1b. See N. Quan, M. Whiteside, and M. Herkenham, "Time course and localization patterns of interleukin-1beta messenger RNA expression in brain and pituitary after peripheral administration of lipopolysaccharide," *Neuroscience*, vol. 83, pp. 281-293, 1998. The amplified IL-1b and other PICs (e.g., IL-1 promotes IL-6 production and release) are then free to bind to their respective receptors in the CNS, effectively conveying an immune system-derived signal to the CNS. See S. M. O'Brien, L. V. Scott, and T. G. Dinan, "Cytokines: Abnormalities in major depression and implications for pharmacological treatment," *Human Psychopharmacology*, vol. 19, pp. 397-403, 2004. The known neural routes of communicating peripheral inflammation or infection to the CNS use the afferent vagal and trigeminal nerve fibers as channels of communication. Sensory afferent fibers are activated by PICs and PAMPs through specialized sensory receptors. Vagal afferents project to the NTS, where intraperitoneal lipopolysaccharide and IL-1b injections were shown to increase glutamate levels in the NTS. See P. Mascarucci, C. Perego, S. Tenazzino et al., "Glutamate release in the nucleus tractus solitarius induced by peripheral lipopolysaccharide and interleukin-1beta," *Neuroscience*, vol. 86, no. 4, pp. 1285-1290, 1998. HPA axis activity is increased via projections from the NTS to the paraventricular nucleus of the hypothalamus. See R. Dantzer, J. C. O'Connor, G. G. Freund et al., "From inflammation to sickness and depression: When the immune system subjugates the brain," *Nature Reviews Neuroscience*, vol. 9, pp. 46-56, 2008.

Within the last decade, Dr. Kevin Tracey and colleagues discovered the previously unrecognized cholinergic anti-inflammatory reflex in the vagus that reflexively releases ACh at the vagal efferent fiber axon terminals in response to inflammation or infection detected by specialized vagal nerve afferents. The reflexive ACh release is directly proportional to levels of certain PICs and PAMPs detected by specialized vagal sensory fibers. See L. V. Borovikova, S. Ivanova, M. Zhang et al., "Vagus nerve stimulation attenuates the systemic inflammatory response to endotoxin," *Letters to Nature*, vol. 405, pp. 458-462, 2000; K. J. Tracey, "The inflammatory reflex," *NATURE*, vol. 420, pp. 853-859, 2002; and T. R. Bernik, S. G. Friedman, M. Ochani et al., "Pharmacological stimulation of the cholinergic antiinflammatory pathway," *J. Exp. Med.*, vol. 195, no. 6, pp. 781-788, 2002. ACh released from vagal efferents was found to bind to the a7nACh receptor, with the effect of suppressing excessive PIC production (e.g., TNF-a, IL-1 and IL-6) at the site of injury or infection or preventing macrophage activation. See K. J. Tracey, "The inflammatory reflex," *NATURE*, vol. 420, pp. 853-859, 2002. The afferent sensing component of the reflex also relays inflammatory signals to the CNS, resulting in I-IPA axis activation, and depending on circulating PIC levels communicated to the CNS via humoral routes, amplification of PICs by activated microglia in the CNS (e.g., IL-1b, TNF-a and IL-6). The PICs then bind to their respective receptors found throughout the CNS, including the limbic system, paralimbic system and hypothalamus, resulting in further HPA axis activation. In a graded fashion, the elevated levels of PICs in the CNS also promote sickness behavior, a mental and physical state characterized by a lack of energy (e.g., lethargy, tiredness, and loss of focus), reduced appetite, depressed mood, anhedonia, anxiety and reduced hygiene/grooming See S. Alesci, P. E. Martinez, S. Kelkar et al., "Major depression is associated with significant diurnal elevations in plasma interleukin-6 levels, a shift of its circadian rhythm, and loss of physiological complexity in its secretion: Clinical implications," *J Clin Endocrinol Metab*, vol. 90, pp. 2522-2530, 2005; R. Dantzer, J. C. O'Connor, G. G. Freund et al., "From inflammation to sickness and depression: When the immune system subjugates the brain," *Nature Reviews Neuroscience*, vol. 9, pp. 46-56, 2008; J. Licinio, and M.-L. Wong, "The role of inflammatory mediators in the biology of major depression: central nervous system cytokines modulate the biological substrate of depressive symptoms, regulate stress-responsive systems, and contribute to neurotoxicity and neuroprotection," *Molecular Psychiatry*, vol. 4, pp. 317-327, 1999; and L. Vitkovic, J. P. Konsman, J. Bockaert et al., "Cytokine signals propagate through the brain," *Molecular Psychiatry*, vol. 5, pp. 604-615, 2000. The cholinergic anti-inflammatory reflex is believed to serve as a fast-acting neural response that helps balance PIC production with the perceived intensity of injury or infection such that pathogens or dead cells are neutralized and scavenged (i.e., the perceived threat of infection or damaged/dead tissue is removed), but healthy cells remain unharmed. An excessive immune response relative to injury or infection intensity, inferred from local PIC levels, can result in excessive phagocytic cell recruitment and activity as well as damage to otherwise healthy tissue. Similarly, an inadequate immune response can result in inadequate phagocytic cell recruitment and activity. In the latter case, infectious bacteria or cancerous cells can multiply, spread, damage otherwise healthy tissues, and potentially lead to toxic shock syndrome, sepsis or terminal cancer. See K. J. Tracey, "The inflammatory reflex," *NATURE*, vol. 420, pp. 853-859, 2002.

Due to the current practice of diagnosing MDD, which typically involves subjective assessments of depressive symptom duration and severity as well as a brief physical exam, refractory MDD may in part be due a chronic disruption of PIC production control mechanisms through the cholinergic anti-inflammatory reflex. If PIC production in response to infection or injury is not adequately balanced by neural and/or humoral anti-inflammatory mechanisms, then PICs can "spill" over into systemic circulation, where they can impart adverse effects on healthy tissues throughout the body, communicate sickness behavior-promoting inflammatory signals to the CNS, and induce many of the symptoms shared by patients displaying sickness behaviors and patients displaying depressive behaviors (e.g., Lethargy/fatigue, anhedonia, depressed mood, an inability to concentrate, sleep disturbances and reduced appetite). See J. M. Cavaillon, C. Munoz, C. Fitting et al., "Circulating cytokines: The tip of the iceberg?," *Circ Shock*, vol. 38, no. 2, pp. 145-152, 1992; R. Dantzer, "Cytokine-induced sickness behavior: Mechanisms and implications," *Annals of New York Academy of Sciences*, vol. 933, pp. 222-234, 2001; and B. L. Hart, "Biological basis of the behavior of sick animals," *Neuroscience & Biobehavioral Reviews*, vol. 12, pp. 123-137, 1988. The non-overlapping symptoms of depression (i.e., Thoughts of worthlessness/guilt and recurrent thoughts of death/suicide) may arise from prolonged, deleterious effects of PICs on CNS neuron health and function. O'Brien et al. (2007) showed that selective serotonin reuptake inhibitor (SSRI)-resistant MDD patients have significantly higher IL-6 and TNF-a levels in blood plasma than healthy controls and SSRI-resistant MDD patients who successfully responded to another class of antidepressants. See S. M. O'Brien, P. Scully, P. Fitzgerald et al., "Plasma cytokine profiles in depressed patients who fail to respond to selective serotonin reuptake inhibitor therapy," *Journal of Psychiatric Research*, vol. 41, pp. 326-331, 2007. They concluded that PIC expression (specifically IL-6 and TNF-a) is higher in refractory MDD patients versus nominal patients and that a failure of PIC suppression is linked to SSRI resistance in refractory MDD patients. Alesci et al., 2005 showed that IL-6 levels are significantly elevated in MDD patients (N=9) versus age and gender matched controls (N=9). In their investigation, patient-reported self-esteem, guilt and suicidal thoughts were significantly correlated with average (over a 24 hr circadian cycle) log-transformed IL-6 levels in circulation. See S. Alesci, P. E. Martinez, S. Kelkar et al., "Major depression is associated with significant diurnal elevations in plasma interleukin-6 levels, a shift of its circadian rhythm, and loss of physiological complexity in its secretion: Clinical implications," *J Clin Endocrinol Metab*, vol. 90, pp. 2522-2530, 2005. Therefore, it seems likely that cytokine-induced sickness behavior from an undiagnosed medical condition (or long-term exposure to an exogenous irritant that causes inflammation) can be misdiagnosed as refractory MDD. The patients then may not respond well to antidepressant drugs, because the source of the depressive symptoms is not targeted. Although this does not imply that VNS is the correct treatment, it is more justified than antidepressant therapy. Since VNS is well suited for modulation of the cholinergic antiinflammatory reflex, which imparts graded anti-inflammatory activity via ACh-a7nAChR mediated suppression of PIC production, and since elevated PIC levels in circulation can induce depressive symptoms in a graded fashion, VNS may similarly reduce depressive symptom severity in a graded fashion. See L. V. Borovikova, S. Ivanova, M. Zhang et al., "Vagus nerve stimulation attenuates the systemic inflammatory response to endotoxin," *Letters to Nature*, vol. 405, pp. 458-462, 2000; K. J. Tracey, "The inflammatory reflex," *NATURE*, vol. 420, pp. 853-859, 2002; K. J. Tracey, "Reflex control of immunity," *Nature Review Immunology*, vol. 9, pp. 418-428, 2009; C. L. Raison, L. Capuron, and A. H. Miller, "Cytokines sing the blues: Inflammation and the pathogenesis of depression," *TRENDS in Immunology*, vol. 27, no. 1, pp. 24-31, 2006; and S. Alesci, P. E. Martinez, S. Kelkar et al., "Major depression is associated with significant diurnal elevations in plasma interleukin-6 levels, a shift of its circadian rhythm, and loss of physiological complexity in its secretion: Clinical implications," *J Clin Endocrinol Metab*, vol. 90, pp. 2522-2530, 2005. The evidence is tantalizing, but the theory has not been tested. To determine whether this theory has merit, the nerve activation clamp (i.e., CAP/SD mapping algorithm with negative feedback) can be used in an endotoxin animal model of sickness behavior (meant to model cytokine-induced depression) to determine whether a relationship exists between the level/rate of efferent vagal nerve fiber activation, ACh release, the level of circulating PICs, and depressive behaviors. The effects of stimulating the afferent arm of the cholinergic anti-inflammatory reflex is expected to reduce HPA axis hyperactivity activity secondary to ACh-a7nAChR mediated suppression of PIC production.

A number of animals (e.g., Wistar-Kyoto rats (250-350 g)) can be used to investigate the role of VNS in reducing depressive/sickness behavior symptom severity and duration with respect to the level/rate of nerve fiber activation. Since the symptoms of cytokine-induced sickness behavior can account for the 9 hallmark symptoms of MDD, and since there exists a high comorbidity of depression in chronically ill patients with disorders associated with long term inflammation (e.g., autoimmune disorders, heart disease, cancer, etc.), treatment-resistant depression may in part be due to excessive or uncontrolled PIC production from a hyperactive immune system, the presence of a persistent infection, chemical or biological stressor, or a failure of negative feedback on PIC production normally provided by GC binding to glucocorticoid receptors (GR) on cells of the immune system (e.g., macrophages, B cells, T cells, etc). See C. L. Raison, L. Capuron, and A. H. Miller, "Cytokines sing the blues: Inflammation and the pathogenesis of depression," *TRENDS in Immunology*, vol. 27, no. 1, pp. 24-31, 2006; S. Alesci, P. E. Martinez, S. Kelkar et al., "Major depression is associated with significant diurnal elevations in plasma interleukin-6 levels, a shift of its circadian rhythm, and loss of physiological complexity in its secretion: Clinical implications," *J Clin Endocrinol Metab*, vol. 90, pp. 2522-2530, 2005; R. Dantzer, and K. W. Kelley, "Twenty years of research on cytokine-induced sickness behavior," *Brain, Behavior, and Immunity*, vol. 21, pp. 153-160, 2007; and R. Dantzer, "Cytokine-induced sickness behavior: Mechanisms and implications," *Annals of New York Academy of Sciences*, vol. 933, pp. 222-234, 2001. If the source of the inflammation is not resolved or controlled over long periods of time, then the immune system may reach a new set point that manifests as depression. The main features of this new set point are 1) a chronically hyper-responsive HPA axis (i.e., stress response system) secondary to diminished GC-mediated negative feedback on CRH, ACTH and GC production, 2) elevated levels of circulating PICs, and 3) a failure of GC-mediated suppression of PIC production. The resulting excess of inflammatory signals is communicated to the CNS by the afferent vagal nerve fibers and/or via the circumventricular organs lining ventricular system of the CNS. This leads to PIC amplification in the CNS. PICs in the CNS then induce PIC type- and level-dependent symptoms of sickness behavior that significantly overlap with the symptoms of MDD. The following hypothesis can be tested: If the cholinergic anti-inflammatory reflex of the vagus nerve serves to reduce excessive PIC release from an overactive immune system, then there should be an associated reduction in depressive/sickness behavior symptom severity due to a decrease in circulating PIC levels. Furthermore, if the cholinergic anti-inflammatory reflex is ineffective, then VNS can be used to modulate its function toward enhanced anti-inflammatory activity and perhaps depressive symptom relief.

Several of the animals can be used for training purposes and to test and debug the automated CAP/SD measurement algorithm. Wistar-Kyoto rats are the strain of choice due to their naturally high level of anxiety, susceptibility to developing depressive behaviors, and natural resistance to antidepressant drugs. See A. Lahmane, C. del Arco, A. Pazos et al., "Are Wistar-Kyoto rats a genetic animal model of depression resistant to antidepressants?," *European Journal of Pharmacology*, vol. 337, pp. 115-123, 1997. The remaining animals can be divided into a control/sham group of a first group of animals and an experimental second group of animals. All the animals in the experimental group and a fraction of animals from the control group can be treated with lipopolysaccharide (an endotoxin derived from gram-negative bacteria) using an intraperitoneal delivery method (10-1000 pg/kg). These animals can serve as an animal model of cytokine-induced depression. See R. Dantzer, and K. W. Kelley, "Twenty years of research on cytokine-induced sickness behavior," *Brain, Behavior, and Immunity*, vol. 21, pp. 153-160, 2007; and R. De La Garza, "Endotoxin- or pro-inflammatory cytokine-induced sickness behavior as an animal model of depression: focus on anhedonia," *Neuroscience and Biobehavioral Reviews*, vol. 29, pp. 761-770, 2005. After a 1-2 week period of daily, low-dose endotoxin injections and close health monitoring, the endotoxin treatment can be temporarily halted. The endotoxin-treated animals in the control/sham group can be used to monitor the effects of implanting a VNS electrode and not stimulating at all. The other animals in the control group can be used to monitor the effects of VNS in the absence of cytokine-induced sickness behavior/depression. These results can be compared to the larger experimental group of animals, where the effects of VNS on acute cytokine-induced depression can be evaluated.

The animals in the experimental group can be further subdivided into multiple groups of several animals each and used to test the effects of VNS on depressive/sickness behavior symptom severity. For each group of animals, the nerve activation level can be maintained at a fixed proportion of maximal activation for the A, B or C fiber types of the vagus nerve (i.e., VNS can be applied such that the stimulus parameters only activate a specific, constant percentage of all A, B or C fibers in the left vagus nerve, respectively). The activation levels that can be maintained are 0, 25, 50 and 100% maximal activation. Within each group, each animal can be started at 0, 25, 50 or 100% maximal activation, but then can be switched to another randomly selected activation level every 2-4 weeks until all activation levels have been applied with the same animal. The endotoxin treatment can resume 2-4 weeks after initiating VNS, and can continue for 4-8 weeks while VNS is applied. The treatment can again be stopped 2-4 weeks before the study endpoint. The purpose of the second round of endotoxin treatment may be to evaluate the effects of VNS on elevated PIC levels and depressive behaviors in the presence of long-term immune activation. Neural recordings (from implanted electrodes in the hippocampus and NTS) can be collected from each animal before stimulation is started, during the stimulation periods at the various nerve activation levels, and right before the animal is terminated from the study for histological analysis. Coincident with the neural recordings, cerebrospinal fluid can be sampled from a cannula implanted in the $4^{th}$ ventricle and/or the left NTS so that PIC, glutamate and GABA level changes can be quantified in response to VNS at various nerve activation levels. Blood samples can be obtained daily in order to track circulating levels of PICs and glucocorticoids. Changes in sucrose preference, weight, grooming and exploratory behavior can be monitored in all animals at the same time that blood and CSF samples are taken. If time permits, an analogous set of VNS experiments can be performed in a kainic acid model of spontaneous seizures. Changes in seizure rate and severity can be tracked in the VNS for TLE experiments.

The stimulation artifact can be reduced by template subtraction, increasing the distance between the stimulating and recording electrodes, or controlling the shape and direction of the cunent flowing between the anode and cathode (e.g., place anode between two cathodes whose potentials are equilibrated using a potentiometer). See D. M. Woodbury, and J. W. Woodbury, "Effects of vagal stimulation on experimentally induced seizures in rats," *Epilepsia*, vol. 31, no. Suppl. 2, pp. S7-S19, 1990. Experience from 2 previous publications by the Center for Implantable Devices on microelectrodes and methods of reducing the foreign-body response to chronic implants has provided an understanding of the challenges that stem from the foreignbody response and methods of overcoming them. See D. B. Jaroch, M. P. Ward, E. Y. Chow et al., "Magnetic insertion system for flexible electrode implantation," *Journal of Neuroscience Methods*, vol. 183, pp. 213-222, 2009; and M. P. Ward, P. Rajdev, C. Ellison et al., "Toward a comparison of microelectrodes for acute and chronic recordings," *Brain Research*, vol. 1282, pp. 183-200, 2009. The CAP/SD algorithm is meant to routinely measure the nerve activation properties so that the stimulus parameter prediction portion of the algorithm remains accurate. Furthermore, the nerve activation clamp is meant to compensate for any mismatch between the stimulus intensity and nerve activation level due to foreign-body response-mediated changes at the electrode-tissue interface. The effects from the clamped nerve fiber group can likely be differentiated from the effects of other nerve fiber types activated in response to the same stimulus through careful experimental design (i.e., If the clamped activation level is treated as a signal of interest and any other nerve fiber activation is treated as noise, then the noise may decrease with increasing animal numbers so that the signal-to-noise ratio is increased). In addition, the utility of the tool can be demonstrated by quantifying candidate biomarker level changes in response to fixed levels/rates of nerve fiber activation. The tool can further be useful if no nerve fiber activation level/rate dependent changes in candidate biomarker levels are found, because it enables the systematic elimination of candidate biomarkers.

After coding and debugging the full algorithm, it can be used to investigate the therapeutic mechanisms of VNS based on discrete levels of A, B or C vagal nerve fiber activation.

In accordance with this disclosure, a nerve activation clamp provides a new type of tool that can be used as an alternative to a voltage or current clamp when working with biological systems.

As illustrated in FIGS. 8A-8F, a nerve activation clamp autonomously varies stimulus amplitude (i.e., intensity) or duration, collectively referred to as stimulus strength, such that the level of activation of one or more neuron types is held constant for any desirable or therapeutically relevant time span. A highly accurate model of how the neuron type(s) of interest collectively respond to any strength of stimulus is autonomously generated by the system, which serves as a guide that enables the system to make a single adjustment to either the pulse amplitude, duration, or the product of amplitude and duration to reach any other level of activation (e.g., the product of amplitude and duration is a charge, in Coulombs, if a constant current stimulus is used). In this context, activation refers to the percentage of all neurons of a particular type, which is defined as the magnitude of the peak at a particular conduction velocity, the peak to peak distance in volts (e.g., if a bipolar or tripolar recording configuration is used to record the nerve/neuron type response), the area of the deflection that gives rise to the peak, or other common metrics used to define activation. The user of this technology turns a dial or enters a desired percentage of maximal activation; the system then determines how to adjust the stimulus intensity and does so without interrupting the ongoing therapy or application.

Neurons rapidly adapt to constant current or voltage stimuli. The effect of the electrical stimulus on the nerve or neuron type of interest is important for therapy, not the electrical stimulus itself. The method described herein enables one to shift from electrical (or similar) stimulus parameters to nerve/nerve fiber activation levels (or a measured effect on an organ, tissue, or system with which the nerve interacts). The apparatus autonomously determines which stimulus parameters to apply, within a predefined safety range, to maintain any percentage of maximal activation or to change to any other percentage of maximal activation. Control is established over the conduits that mediate effects on organs, tissues, or systems with which the nerve interacts; by extension, control is established over the activity of these same tissues.

The system continually updates its model, as the magnitude of individual neuron responses within a specific class/type of neuron may vary due to exogenous and endogenous factors (e.g., Increased sodium intake, hypothermia, hyperthermia, an effect of a drug, or other factors). These recursive updates continually ensure that the model/nerve activation profile not only adapts to minute changes in nerve/neuron type responses over time, but that it also becomes more accurate as the number of applied stimuli increases over time.

The system can also use negative feedback (in the form of a difference between the expected magnitude of the response and the actual magnitude of the response) to incrementally adjust stimulus strength to more precisely determine the stimulus parameters that yield the desired activation level of the desired neuron type(s) within a nerve. This helps maximize the accuracy of the nerve activation profile.

In general, this invention works with any i) stimulation system (or similar) and uses ii) transducers (e.g., metallic electrodes) to recruit and record a nerve response (as a voltage signal) and iii) a microprocessor (or similar) to run the system and other features of the technology. In some embodiments, other technology may be incorporated, such as wireless transmission circuitry for external communication with the system and wireless recharging circuitry to recharge batteries (or similar) that power the system.

Stimulation and recording electrodes can be one of the following: a cuff electrode or similar (which makes circumferential contact with the nerve trunk or branch); a surface pad electrode or similar (which is placed on the skin); a microwire electrode or similar (which is placed in direct or near direct contact with the nerve trunk or branch), or the like.

The nerve trunk or branch can be stimulated with: one transducer on or near the nerve (monopolar configuration); two transducers on or near the nerve (bipolar configuration); three or more transducers on or near the nerve (e.g., tripolar configuration); constant current or voltage pulses of any shape, especially rectangular pulses; or monophasic or charge-balanced biphasic/triphasic stimuli.

The compound action potential/nerve response can be recorded from the nerve trunk or branch with: one transducer on or near the nerve (single-ended configuration); two transducers on or near the nerve (differential configuration); three or more transducers on or near the nerve (e.g., tripolar configuration); surface pad electrodes (or similar), or the like. The recording transducers may be placed at a fixed or measurable distance from the stimulating cathode to ensure that the conduction velocity of the different neuron types within a nerve can be readily measured (e.g., by dividing the transducer/electrode separation distance by the latency of a peak/feature in the compound action potential waveform). The signal recorded from the nerve can be processed with: a microprocessor (or similar); an ASIC; an external controller (in an alternative embodiment of the invention); or the like.

The invention described herein enables control of a single neuron type within a nerve or simultaneous control of two or more neuron types within a nerve. The latter is possible when regions of the nerve activation profiles, generated by the system for each fiber type within a nerve, overlap.

Simultaneous control of two or more neuron types within a nerve is useful, for example, when activation of one neuron type is therapeutic, but activation of one or more other neuron types generates unwanted side effect(s). In this case, a physician, researcher, or patient can select a different point within the region of overlap that provides the same activation level for the neuron type that drives the therapy, but reduces the activation level of the neuron type(s) responsible for the unwanted side effect(s).

The method and apparatus described herein serves as a common dosing platform for all uses of neuromodulation therapy, especially nerve stimulation therapy, using percentage of maximal nerve/neuron type activation as a dose. Activation of a particular neuron type cannot be adequately measured or maintained with currently available methods and technology. Each patient, nerve and neuron type respond differently to the same strength and type of stimulus. The nerve input to central or peripheral tissues, organs, or systems, as well as subsequent effects on these tissues, organs, or systems, mediates the quality and efficacy of neuromodulation therapy, not the strength of a constant voltage or current stimulus. This method and apparatus works on any neuron type in any nerve of any patient. The method and apparatus described herein enables prediction and maintenance of any level of nerve/neuron type activation for any length of time.

Activation of a particular neuron type cannot be predicted with currently available methods. The unique "Rheobase Current versus Percent Maximal Activation Relationship" as well as the described method of using the charge-duration line enables accurate prediction of nerve/neuron type activation to any applied stimulus pulse. The method and apparatus enables rapid switching between nerve/neuron type activation levels without a need to perform a tedious stimulus parameter/nerve response search. Using linear regression and feedback from the nerve, in the form of a compound (nerve or muscle) action potential, the algorithm autonomously updates its model over time to ensure improved prediction accuracy and adaptation to natural or deliberate changes in the patient's physiology over time.

The method and apparatus applies to other forms of neuro-modulation as well, such as non-invasive stimulation (all forms of neuromodulation, especially electrical stimulation), drug/chemical stimulation, optical/optogenetic stimulation, acoustic/ultrasonic stimulation and/or other forms of stimulation The method and apparatus supports closed-loop system development since it is a platform that controls nerve/neuron type activation. For example, any biological marker (e.g., electrocardiogram, electrogastrogram, electromyogram, neurotransmitter changes, gene expression changes, etc.) can be fed into the algorithm as an input. It can be programmed to use any number of these types of input as control points for determining how and when to change the nerve/neuron type activation levels (or other parameters such as pulse repetition frequency). This method and apparatus comes with a dosing ability and control.

Figure 9:
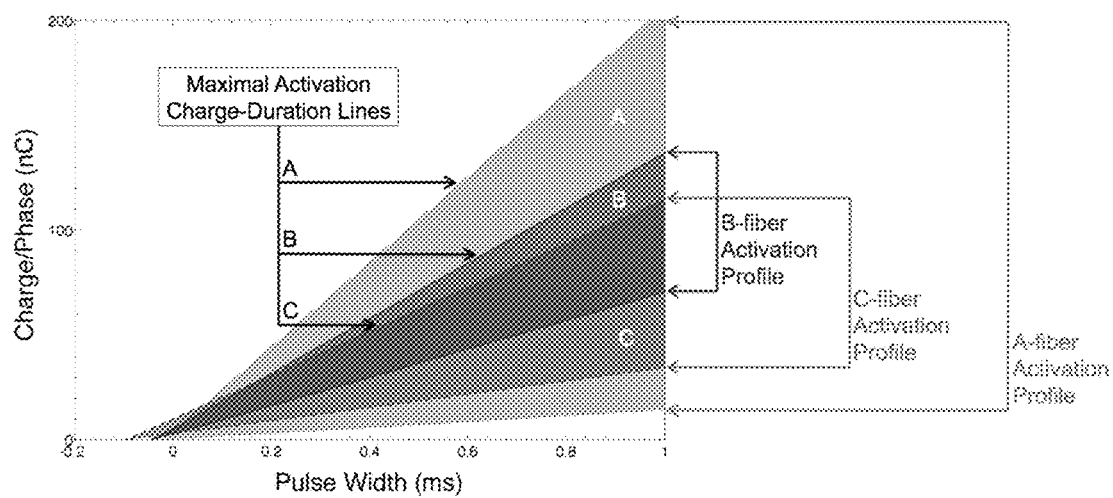
FIG. 9 illustrates an overlaid nerve activation profile for A, B, and C fiber types.

FIG. 9 illustrates an overlaid "Nerve Activation Profile" for A, B and C fiber types. These nerve activation profiles were predicted by the algorithm using data collected from the vagus nerve of an adult female Long-Evans rat. It is important to note that this type of profile is unique to the subject, nerve and neuron types within that nerve; this particular profile therefore only applies to the subject and nerve from which the data used to construct the model was collected. However, the method applies to any neuron type in any nerve of any subject using electrical stimulation or other form of neuromodulation, such as chemical stimulation, optical stimulation, or acoustic stimulation. The activation profile for each fiber type (i.e., neuron type) has an upper boundary formed by the charge-duration line that represents maximal activation and a lower boundary formed by the charge-duration line that represents the threshold for any activation (i.e., 0% maximal activation). The key to predicting the charge-duration lines for all levels of maximal activation (i.e., 0-100%), which represent all of the stimulus pulse amplitude and duration pairs that yield the same level of maximal activation, and the key to predicting how a nerve/neuron type will respond to any stimulus with a given duration (e.g., Current pulse duration) and intensity (e.g., Current amplitude), lies in the slope-activation relationship—otherwise known as the "Rheobase Current versus Percent Maximal Activation Relationship." First, the algorithm autonomously searches for stimulus pulse amplitudes and durations that yield maximal activation of A, B, or C fiber types, which is defined as the point where an increase in stimulus strength no longer produces an increase in the magnitude of the compound action potential response. This process is repeated for 2 or more different pulse widths. Next, all of the stimulus-response data is pooled, and stimulus pulse amplitude and duration pairs that evoked the same level of maximal activation are grouped. Using groups that have 2 or more different pulse widths represented, charge-duration lines are constructed using linear regression. The slope of these lines is the rheobase current, while the x-intercept is the strength-duration time constant, $\tau_{SD}$. The slopes of the charge-duration lines for each level of maximal activation are then plotted against the corresponding percent maximal activation. The data is then converted to a linear form using a logarithmic transform, typically a natural logarithm, but base 10 logarithms and others apply.

Next, linear regression is used to obtain an optimal fit to the data. This best-fit equation is the "Rheobase Current versus Percent Maximal Activation Relationship," and can be used to predict the slope of any level of maximal activation. Since the strength-duration time constant is relatively constant for most levels of maximal activation, one now has the ability to reconstruct charge-duration lines for any level of maximal activation. One can perform a similar fit to a plot of "Strength-duration time constant versus Percent Maximal Activation," although is of less importance than the "Rheobase Current versus Percent Maximal Activation Relationship."

Figure 10:
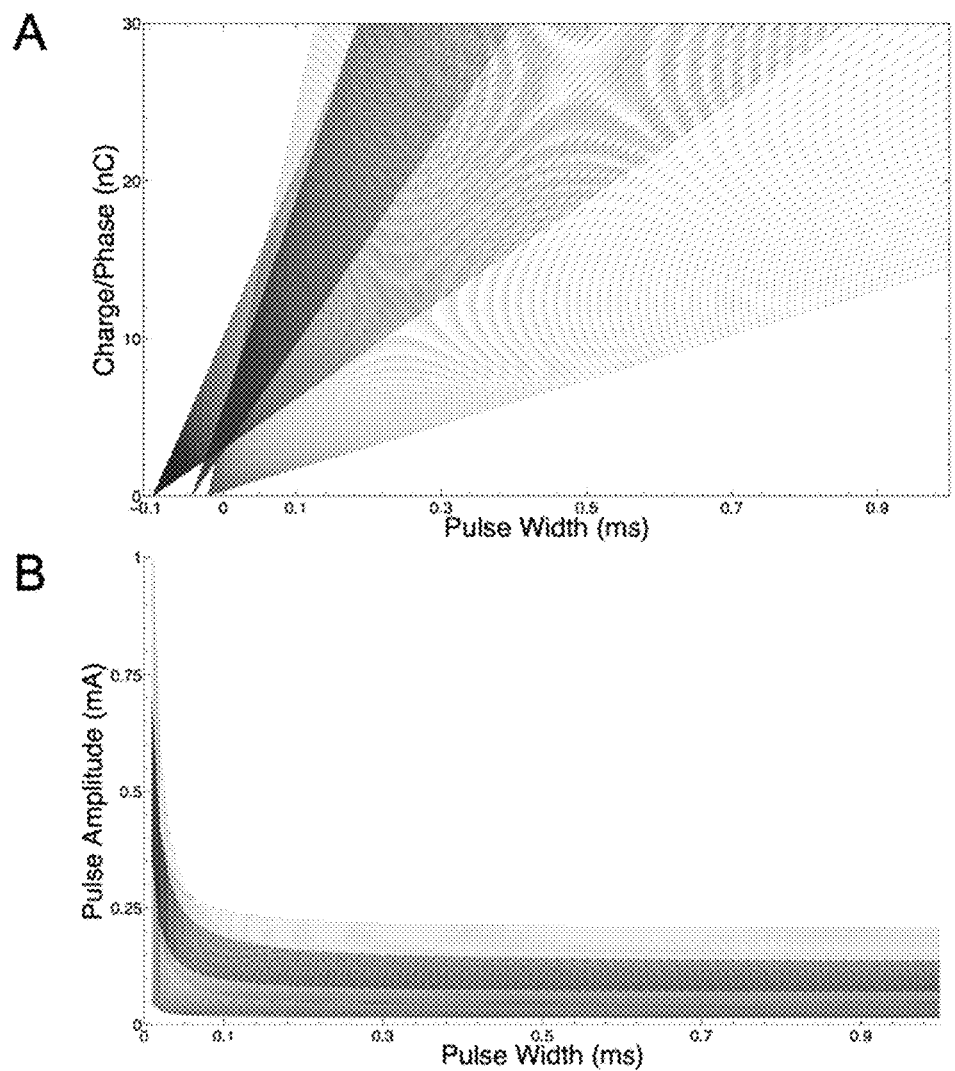
FIG. 10 illustrates overlaid stimulus-response profiles for A, B, and C fiber types.

FIG. 10 illustrates overlaid stimulus-response profiles for A, B and C fiber types. Profiles were created using the methods outlined in this application and data collected from the left vagus nerve of an adult female Long-Evans rat. A) Charge-duration lines for $\{0, 1, 2, \ldots, 100\}$% maximal A, B and C fiber activation. Each charge-duration line represents an infinite number of stimulus pulse amplitude and duration combinations that yield the particular level of activation represented by the line. Grey lines are for A fiber types, red lines are for B fiber types, and blue lines are for C fiber types. Activation level increases with the slope of the line, as predicted by the algorithm. Note the common x-intercept for each activation profile; it represents the strength-duration time constant, $\tau_{SD}$, for each fiber type. From most negative to least negative, the strength-duration time constants are shown for C, B and A fiber types. B) Strength-duration curves reconstructed from charge-duration lines predicted for $\{0, 1, 2, \ldots, 100\}$% maximal A, B and C fiber activation. This is the same data shown in A, but in a more commonly used format. It is obtained by dividing each point on the charge-duration line by its corresponding duration.

Figure 11:
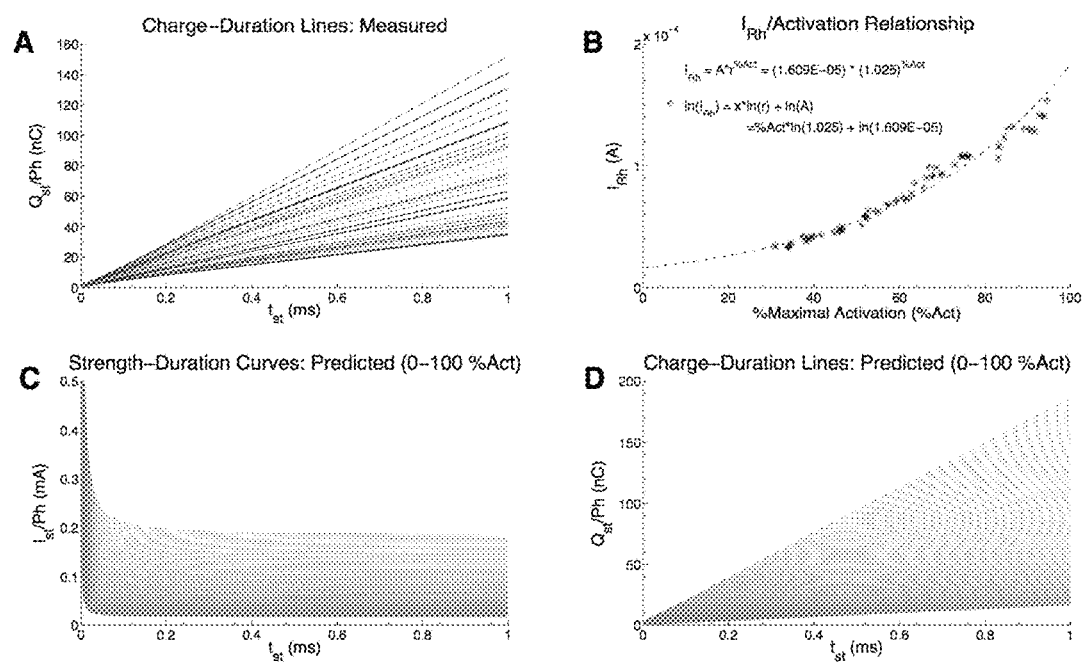
FIG. 11 illustrates a summary of a nerve activation profile creation process.

FIG. 11 illustrates a summary of nerve activation profile creation process. This model was generated using A-fiber stimulus-response data collected from a female Long-Evans rat. A) Charge-duration lines created from stimulus-response data collected while the algorithm autonomously searches for the compound action potential voltage corresponding to maximal fiber activation. This voltage value is used as a normalizing factor. Activation level increases with slope. B) The "Rheobase Current versus Percent Maximal Activation Relationship," including the rheobase current values corresponding to the charge-duration line slopes in A) and the best-fit curve obtained using linear regression of log-transformed data. The best-fit equations are shown in logarithmic and linear forms. C) Predicted strength-duration curves for $\{0, 1, 2, \ldots, 100\}$% maximal fiber activation. D) Predicted charge-duration lines for $\{0, 1, 2, \ldots, 100\}$% maximal fiber activation. This data is analogous to that presented in C), and is formed by multiplying each amplitude shown in C) by its corresponding duration and then plotting the resulting charge, Q, against the same duration.

Figure 12:
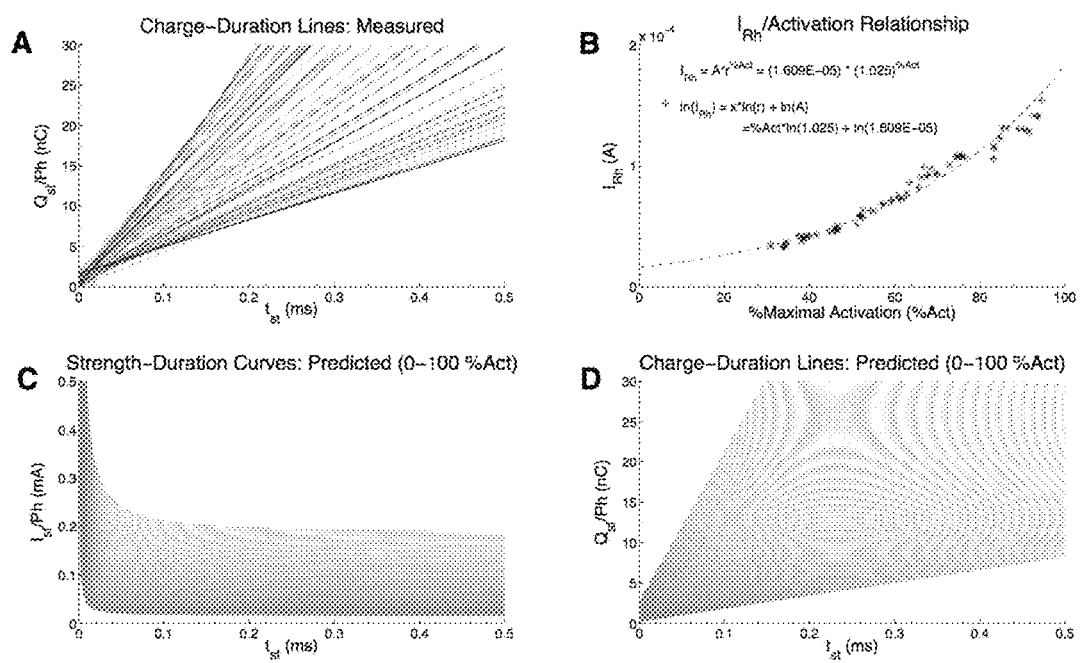
FIG. 12 illustrates a closer view of data presented in FIG. 11.

FIG. 12 illustrates a closer view of the data presented in the preceding FIG. 11.

Figure 13:
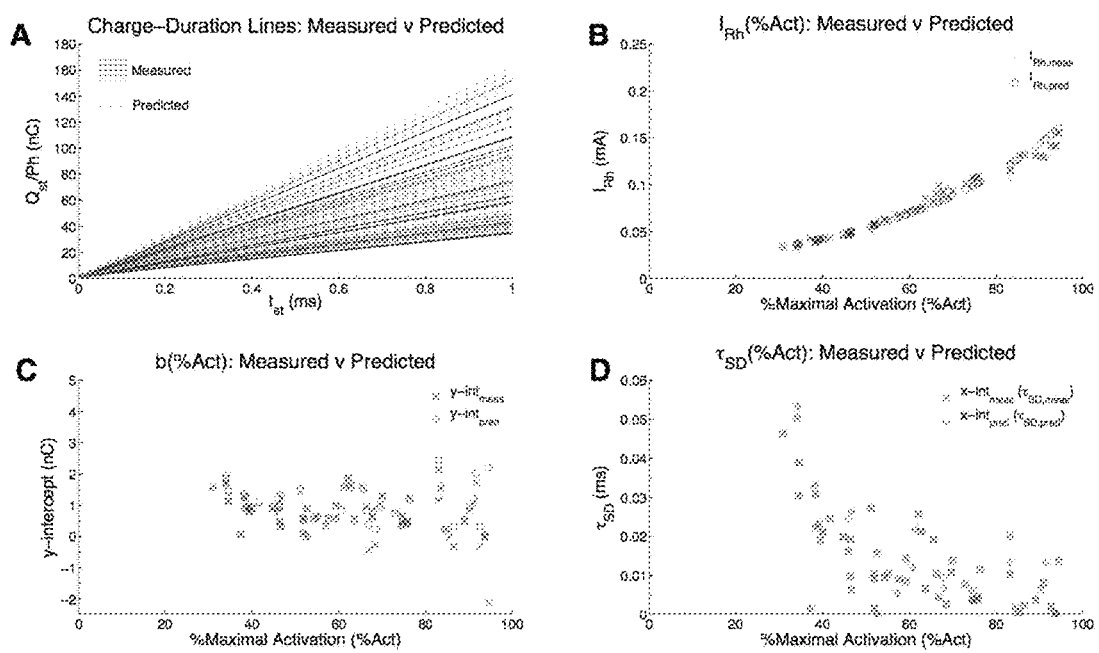
FIG. 13 illustrates a summary of a nerve activation profile creation process, and accuracy of subsequent charge-duration line predictions.

FIG. 13 illustrates a summary of nerve activation profile creation process and the accuracy of subsequent charge-duration line predictions. This model was generated using A-fiber stimulus-response data collected from a female Long-Evans rat. A) Charge-duration lines created from stimulus-response data collected while the algorithm autonomously searches for the compound action potential voltage corresponding to maximal fiber activation. Charge-duration lines constructed using measured stimulus-response data are plotted in color, while charge-duration lines predicted using the nerve activation profile and algorithm-generated model are plotted as grey dashed lines. All data necessary to create this model was collected autonomously in under 5 minutes, yielding a highly accurate model. As therapy is delivered or more data is collected, the model becomes more accurate as the additional data is incorporated. B) Measured versus predicted rheobase current values showing a highly accurate prediction across the range of possible activation values. C) Measured versus predicted y-intercept values, which are used to predict the strength-duration time constant (i.e., the x-intercept, otherwise referred to here as $\tau_{SD}$). D) Measured versus predicted strength-duration time constants, which are either predicted directly from measured data using linear interpolation, modeled with regression-based methods (for predictive purposes), or replaced with a mean value (when little data is available).

Figure 14:
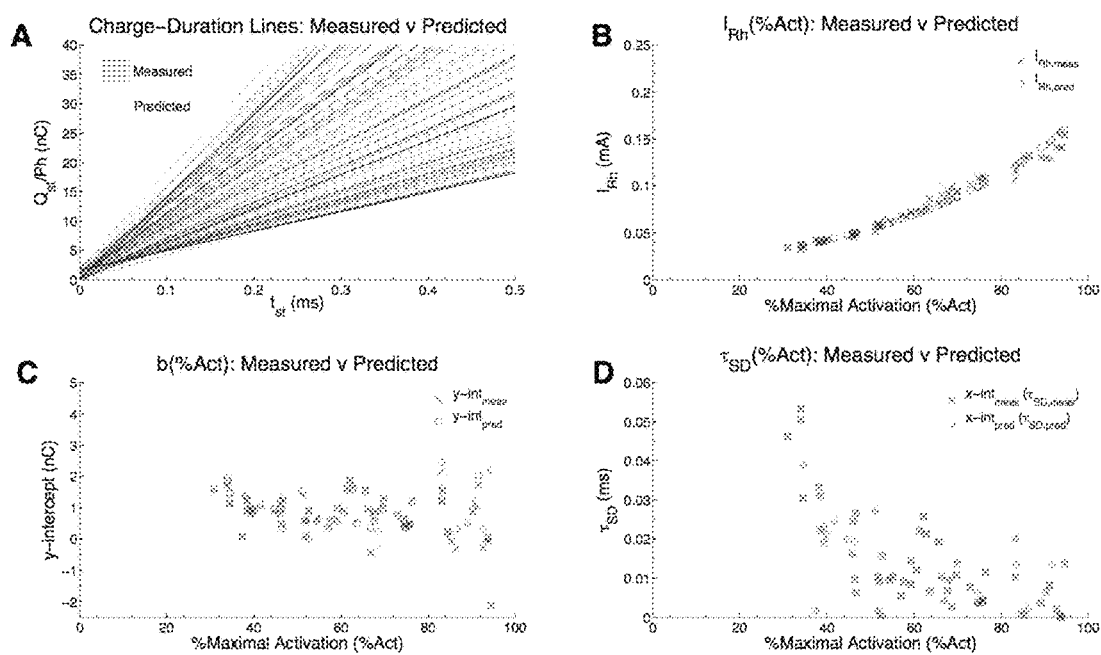
FIG. 14 illustrates a closer view of data presented in FIG. 13.

FIG. 14 illustrates a closer view of the data presented in FIG. 13.

Those skilled in the art will recognize that numerous modifications can be made to the specific implementations described above. Therefore, the present disclosure is not to be limited to the specific embodiments illustrated and described above.

The invention claimed is:

1. An apparatus for activating one or more neurons in a patient at a desired activation level for a therapeutic purpose comprising:

a transducer for stimulating the one or more neurons according to a set of stimulus parameter values;

a measuring electrode configured to measure an activation level yielded by the stimulation of the one or more neurons, the activation level representing at least one of (1) a percentage of activated neurons inside a nerve, (2) a percentage activation of organ function, or (3) a percentage inhibition of organ function;

a neuron activation comparator for comparing the measured activation level of the one or more neurons to the desired activation level of the one or more neurons; and a closed-loop micro controller configured to autonomously predict, at a microprocessor, a particular set of stimulus parameter values to apply to form a stimulation pulse shape yielding the desired activation level representing a particular non-zero percentage of a particular non-zero percentage of at least one of (1) activated neurons inside a nerve, (2) organ function, or (3) inhibition of organ function, the closed-loop micro controller is configured to autonomously derive the predicted set of stimulus parameter values to apply from measured patient characteristics, the closed-loop micro controller is configured to autonomously generate an activation profile of one or more neuron types based on a measured physiological response to the stimulation according to the predicted set of stimulus parameter values, the generated activation profile comprises, for each of two or more particular non-zero activation levels of each of the one or more neuron types, a plurality of sets of stimulus parameter values observed or predicted to yield the particular non-zero activation level, the closed-loop micro controller is configured to autonomously derive the measured patient characteristics via a linear regression from at least one of (1) measurements by the measuring electrode of the activation level of each of the one or more neuron types for different electrical pulse durations and amplitudes and (2) measurements of organ function for different electrical pulse durations and amplitudes, the closed-loop micro controller is configured to actively maintain the desired activation level at the particular non-zero percentage by adjusting the predicted set of stimulus parameter values to apply to stimulate the one or more neurons, the closed-loop micro controller applies changes to the activation profile of the one or more neuron types over time based on the adjusted set of stimulus parameter values and is configured to adapt to the changes in the activation profile of the one or more neuron types to maintain the desired activation level by autonomously updating the measured patient characteristics based on at least one of (1) additional measurements by the measuring electrode of the activation level of each of the one or more neuron types for different electrical pulse durations and amplitudes and (2) additional measurements of organ function for different electrical pulse durations and amplitudes.

2. The apparatus of claim 1 wherein the one or more neurons correspond to a particular neuron type to be stimulated via the transducer.

3. The apparatus of claim 1 wherein the one or more neurons comprise a plurality of neuron types and the measuring electrode measures the activation level of each of the neuron types.

4. The apparatus of claim 1 wherein the one or more neurons are at least one of a vagus nerve, cranial nerve, peripheral nerve and spinal nerve.

5. The apparatus of claim 1 wherein the one or more neurons are stimulated by modulating the shape of a current stimulation pulse.

6. The apparatus of claim 1 wherein the one or more neurons are stimulated by modulating the shape of a voltage stimulation pulse.

7. The apparatus of claim 1 wherein the stimulation pulse shape is autonomously adjusted, within a defined safety range, to maintain the activation level of the one or more neurons at the particular non-zero percentage.

8. The apparatus of claim 1 including a sensor for sensing a level of a biological marker and wherein the closed-loop micro controller adjusts and maintains the desired activation level of the one or more neurons at the particular non-zero percentage based at least in part upon the sensed level of the biological marker.

9. The apparatus of claim 8 wherein the biological marker comprises one of an electrocardiogram, electrogastrogram, electromyogram, neurotransmitter change, or gene expression change.

10. The apparatus of claim 1 wherein the closed-loop micro controller includes an electronic memory to collect and store data over time regarding a relationship between one or more activation levels and sets of stimulus parameter values.

11. The apparatus of claim 1 wherein the stimulation is one of electrical stimulation, drug/chemical stimulation, optical/optogenetic stimulation and acoustic/ultrasonic stimulation, optimized based on patient characteristics.

* * * * *